US012624351B2

(12) United States Patent
Nguyen et al.

(10) Patent No.: US 12,624,351 B2
(45) Date of Patent: May 12, 2026

(54) REAL-TIME DETECTION OF ERRORS IN OLIGONUCLEOTIDE SYNTHESIS

(71) Applicant: MICROSOFT TECHNOLOGY LICENSING, LLC, Redmond, WA (US)

(72) Inventors: Bichlien Hoang Nguyen, Seattle, WA (US); Jake Smith, Seattle, WA (US); Karin Strauss, Seattle, WA (US); Robert Carlson, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1303 days.

(21) Appl. No.: 17/325,108

(22) Filed: May 19, 2021

(65) Prior Publication Data

US 2022/0372468 A1      Nov. 24, 2022

(51) Int. Cl.
*C12N 15/10*      (2006.01)
*G01N 21/64*      (2006.01)
*G01N 27/327*      (2006.01)

(52) U.S. Cl.
CPC ..... *C12N 15/1065* (2013.01); *C12N 15/1072* (2013.01); *G01N 21/6428* (2013.01);
(Continued)

(58) Field of Classification Search
None
See application file for complete search history.

(56) References Cited

U.S. PATENT DOCUMENTS 5,763,594 A      6/1998 Hiatt et al.
6,232,465 B1      5/2001 Hiatt et al.
(Continued)

FOREIGN PATENT DOCUMENTS

WO      WO-02074988 A2 * 9/2002 ............. B82Y 30/00
WO      WO-2011150168 A1 * 12/2011 ......... C12N 15/1068
(Continued)

OTHER PUBLICATIONS

Palluk, S., Arlow, D. H., De Rond, T., Barthel, S., Kang, J. S., Bector, R., . . . & Keasling, J. D. (2018). De novo DNA synthesis using polymerase-nucleotide conjugates. Nature biotechnology, 36(7), 645-650. (Year: 2018).*
(Continued)

*Primary Examiner* — Kaitlyn L Minchella
*Assistant Examiner* — Noah A. Auger
(74) *Attorney, Agent, or Firm* — Benjamin Keim; Newport IP, LLC

(57) ABSTRACT

Fluorophores are used during the synthesis of oligonucleotides to achieve real-time quality control of the synthesis process. Fluorescence may indicate successful addition of individual nucleotides to a growing oligonucleotide strand or removal of a blocking group. The oligonucleotides may be created by enzymatic synthesis using terminal deoxynucleotidyl transferase (TdT). The synthesis is performed on an addressable array so that oligonucleotides with different sequences are created in parallel on different regions of the array. The oligonucleotide sequences are predetermined and the locations of synthesis on the array are controlled. Observed fluorescence is compared to expected locations of fluorescence as determined by the oligonucleotide sequences and the arrangement on the array. Thus, the fidelity of oligonucleotide synthesis is checked as synthesis proceeds. If a variation is found, a mitigating action is taken (Continued)

such as repeating addition of a species of nucleotide or repeating a deblocking step.

19 Claims, 8 Drawing Sheets

(52) U.S. Cl.
CPC ..... *G01N 21/6456* (2013.01); *G01N 27/3277* (2013.01); *G01N 2021/6439* (2013.01)

(56) References Cited

U.S. PATENT DOCUMENTS

| | | | | |
|---|---|---|---|---|
| 7,223,541 | B2 * | 5/2007 | Fuller | C09B 11/24 |
| | | | | 435/5 |
| 7,279,563 | B2 | 10/2007 | Kwiatkowski | |
| 7,414,116 | B2 | 8/2008 | Milton et al. | |
| 7,541,444 | B2 | 6/2009 | Milton et al. | |
| 8,133,669 | B2 | 3/2012 | Lebedev et al. | |
| 10,059,929 | B2 | 8/2018 | Efcavitch et al. | |
| 2003/0224387 | A1 * | 12/2003 | Kunwar | B82Y 15/00 |
| | | | | 205/777.5 |
| 2006/0134638 | A1 * | 6/2006 | Mulligan | C12Q 1/6827 |
| | | | | 435/6.1 |
| 2006/0275927 | A1 * | 12/2006 | Dubin | B01J 19/0046 |
| | | | | 438/1 |
| 2010/0130368 | A1 * | 5/2010 | Balasubramanian | |
| | | | | C12Q 1/6837 |
| | | | | 506/7 |
| 2013/0005612 | A1 | 1/2013 | Carr et al. | |
| 2019/0062804 | A1 | 2/2019 | Church et al. | |
| 2019/0136312 | A1 * | 5/2019 | Mir | C12Q 1/6874 |
| 2020/0199662 | A1 | 6/2020 | Strauss et al. | |
| 2020/0384434 | A1 | 12/2020 | Nguyen et al. | |
| 2021/0071170 | A1 | 3/2021 | Nguyen et al. | |

FOREIGN PATENT DOCUMENTS

| | | | | |
|---|---|---|---|---|
| WO | 2017223517 | A1 | 12/2017 | |
| WO | WO-2020020608 | A1 * | 1/2020 | B01J 19/0046 |

OTHER PUBLICATIONS

Fuller, C. W., Middendorf, L. R., Benner, S. A., Church, G. M., Harris, T., Huang, X., . . . & Vezenov, D. V. (2009). The challenges of sequencing by synthesis. Nature biotechnology, 27(11), 1013-1023. (Year: 2009).*

Pfeiffer, F., Gröber, C., Blank, M., Händler, K., Beyer, M., Schultze, J. L., & Mayer, G. (2018). Systematic evaluation of error rates and causes in short samples in next-generation sequencing. Scientific reports, 8(1), 10950. (Year: 2018).*

Carr, P. A., Park, J. S., Lee, Y. J., Yu, T., Zhang, S., & Jacobson, J. M. (2004). Protein-mediated error correction for de novo DNA synthesis. Nucleic acids research, 32(20), e162-e162. (Year: 2004).*

"International Search Report and Written Opinion Issued in PCT Application No. PCT/US22/026423", Mailed Date: Aug. 4, 2022, 13 Pages.

"Quencher-labeled Adenosines", Retrieved from: https://www.jenabioscience.com/nucleotides-nucleosides/nucleotides-by-structure/fluorescent-nucleotides/adenosines-quencher-labeled, Jan. 20, 2021, 3 Pages.

Bi, et al., "Building Addressable Libraries: The Use of "Safety-Catch" Linkers on Microelectrode Arrays", In Journal of the American Chemical Society vol. 132, Issue 49, Nov. 19, 2010, pp. 17405-17407.

Calvert, Paul, "Inkjet Printing for Materials and Devices", In Journal of Chemistry of materials, vol. 13, Issue 10, Oct. 15, 2001, pp. 3299-3305.

Chen, et al., "The History and Advances of Reversible Terminators Used in New Generations of Sequencing Technology", In Journal Genomics, Proteomics & Bioinformatics, vol. 11, Issue 1, Feb. 2013, pp. 34-40.

Drmanac, et al., "CoolMPSTM: Advanced massively parallel sequencing using antibodies specific to each natural nucleobase", In Journal of BioRxiv, Feb. 20, 2020., pp. 1-19.

Egeland, et al., "Electrochemically Directed Synthesis of Oligonucleotides for DNA Microarray Fabrication", In Journal of Nucleic Acids Research, vol. 33, Issue 14, Aug. 5, 2005, pp. 1-7.

Fu, et al., "Small-Molecule Fluorescent Probes and Their Design", In Journal of RSC Advances, vol. 8, Aug. 14, 2018, pp. 29051-29061.

Winz, et al., "Nucleotidyl Transferase Assisted DNA Labeling with Different Click Chemistries", In Journal of Nucleic Acids Research, 2015, vol. 43, No. 17, May 26, 2015, pp. 1-10.

Guerra, Cesare., "Analysis Of Oligonucleotide Microarrays By 3' End Labeling using Fluorescent Nucleotides and Terminal Transferase", In Journal of BioTechniques, vol. 41, No. 1, Jul. 2006, pp. 53-56.

Hiwang, Gil Tae, "Single-Labeled Oligonucleotides Showing Fluorescence Changes upon Hybridization with Target Nucleic Acids", In Journal of Molecules, vol. 23, Issue 1, Jan. 8, 2018, 19 Pages.

Kricka, et al., "Analytical Ancestry: "Firsts" in Fluorescent Labeling of Nucleosides, Nucleotides, and Nucleic Acids", In Journal of Clinical Chemistry, vol. 55, Issue 4, Apr. 1, 2009, pp. 670-683.

Kumar, et al., "Terminal Phosphate Labeled Nucleotides: Synthesis, Applications, and Linker Effect on Incorporation by DNA Polymerases", In Journal of Nucleosides, Nucleotides & Nucleic Acids, vol. 24, Issue 5-7, Nov. 15, 2011, pp. 401-408.

Levine, et al., "Real-Time, Multiplexed Electrochemical DNA Detection using an Active Complementary Metal-Oxide-Semiconductor Biosensor Array with Integrated Sensor Electronics", In Journal of Biosens Bioelectron, vol. 24, Issue 7, Mar. 15, 2009, pp. 1-16.

Lubin, et al., "Effects of Probe Length, Probe Geometry, and Redox-Tag Placement on the Performance of the Electrochemical E-DNA Sensor", In Journal of Analytical Chemistry, vol. 81, Issue 6, Mar. 15, 2009, pp. 2150-2158.

Metzker, et al., "Termination of DNA Synthesis by Novel 3'-Modified-deoxyribonucleoside 5'-Triphosphates", In Journal of Nucleic Acids Research, vol. 22, Issue 20, Oct. 1994, pp. 4259-4267.

Monroy-Contreras, et al., "Molecular Beacons: Powerful Tools for Imaging RNA in Living Cells", In Journal of Nucleic Acids, Aug. 22, 2011, pp. 1-16.

Palluk, et al., "De Novo DNA Synthesis Using Polymerase-Nucleotide Conjugates", In Journal of Nature Biotechnology, vol. 36, Issue 7, Jul. 2018, 11 Pages.

Thai, et al., "Distinct and Opposite Activities of Human Terminal Deoxynucleotidyltransferase Splice Variants", In the Journal of Immunology, vol. 173, Issue 6, Sep. 15, 2004, pp. 4009-4019.

Willsey, et al., "Puddle: A Dynamic, Error-Correcting, Full-Stack Microfluidics Platform", In Proceedings of the Twenty-Fourth International Conference on Architectural Support for Programming Languages and Operating Systems, Apr. 13, 2019, pp. 183-197.

\* cited by examiner

REAL-TIME DETECTION OF ERRORS IN OLIGONUCLEOTIDE SYNTHESIS

BACKGROUND

Oligonucleotides may be synthesized for many reasons such as for use in basic scientific research, for medical applications, and even to encode digital data. There are many techniques for synthesizing oligonucleotides. One technique is enzymatic synthesis which uses a template-independent DNA polymerase such as terminal deoxynucleotidyl transferase (TdT). Any technique for oligonucleotide synthesis can introduce errors. If an error is introduced in de novo synthesis, the sequence of the oligonucleotide that is actually created is not the same as the intended sequence. Errors can include addition of an incorrect nucleotide or failure to add a nucleotide.

Errors may cause experiments to fail, prevent a medical use from providing a benefit to a patient, or result in storage of incorrect digital data. Techniques for checking errors generally require sequencing of the oligonucleotides after synthesis is complete. Thus, synthesis errors are not detectable, if at all, until later in a process. If errors are systemic or widespread, an entire batch of oligonucleotides may be unusable. Continuing to create oligonucleotides when there is a systemic problem or high error rate may waste valuable reagents. For digital data storage applications, if the original data is not recorded elsewhere, errors in synthesis can result in a complete loss of data.

Accordingly, it would be advantageous if there were a way to detect errors in real-time during synthesis of oligonucleotides. The following disclosure is made with respect to these and other considerations.

SUMMARY

This disclosure provides techniques that use physically detectable tags such as fluorophores to monitor steps in the synthesis of oligonucleotides or other polymers and identify variations that may indicate an error in synthesis. The oligonucleotides are synthesized using solid-phase techniques on the surface of an addressable array. The intended sequences of the oligonucleotides to be synthesized are known in advance. The addressable array controls the location of oligonucleotide growth so that oligonucleotides of different sequences may be synthesized on different portions of the same array. This technique can create a batch of oligonucleotides with different sequences. The addressable array may be implemented as a microelectrode array that has a large number of individually controllable electrodes.

The sequences of the oligonucleotides and the locations where each oligonucleotide is created are used to determine where the physically detectable tags are expected in each round of synthesis. The specific event that results in detection of a physically detectable tag will vary with the type of tag and design of the synthesis system. In one implementation, nucleotides labeled with a fluorescent blocking group may be added to extend a growing oligonucleotide. Incorporation of the labeled nucleotides at specific locations on the addressable array can be detected by fluorescence. Deblocking before addition of another nucleotide can then be detected by a loss of fluorescence.

The locations on the addressable array where the physically detectable tags are detected are compared to expected locations derived from the sequences of the oligonucleotides and the locations of synthesis. If there is a variation, such as not detecting fluorescence at a location on the addressable array where it was expected, this may trigger a mitigating action. The mitigating action may be abandonment of the synthesis run. Stopping further synthesis when there are errors can prevent wasting reagents. Alternatively, synthesis may be modified to correct or mitigate the error. For example, if expected fluorescence resulting from incorporation of nucleotides was not detected, the same species of nucleotide may be added again. Any variation from expected behavior may also be recorded in metadata that can be associated with the oligonucleotides once synthesis is complete. The metadata may include information such as the types and numbers of variations.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

DETAILED DESCRIPTION

This disclosure provides techniques for real-time observation of polymer synthesis by use of physically detectable tags that are incorporated during synthesis. The physically detectable tags provide a way to observe the chemical reactions of a synthesis process. Solid-phase polymer synthesis on an addressable array is combined with sequencing of the polymer. Thus, as a polymer is created de novo by sequential addition of polymer subunits the polymer is also sequenced. The observed sequence is compared to the intended sequence to identify variations that may indicate errors. In some implementations, the physically detectable tags do not provide explicit sequence information but can be used to validate successful completion of a step in the synthesis process. Knowledge of potential errors during synthesis provides many options for mitigation of the errors.

Figure 1:
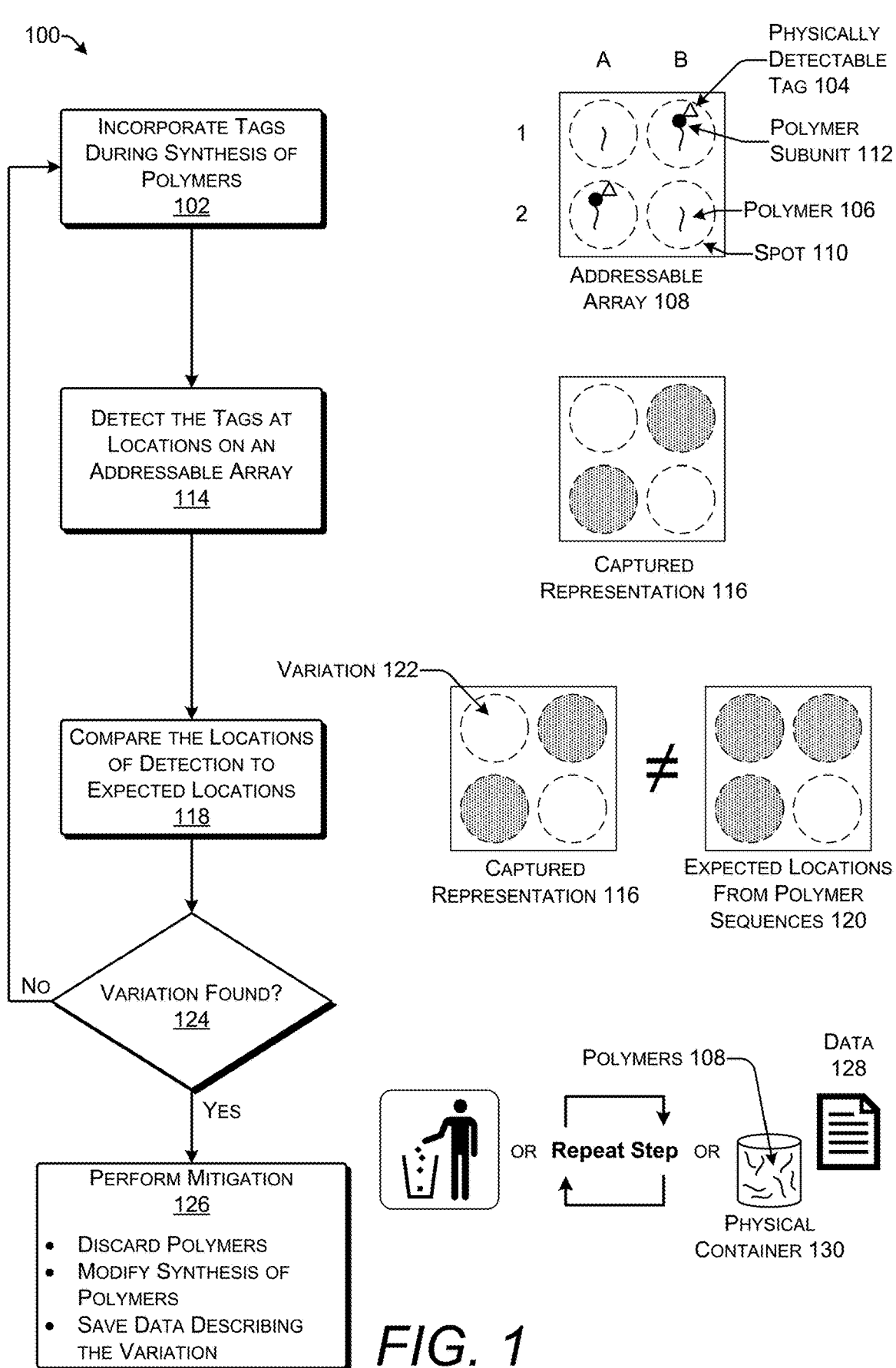
FIG. 1 is a flow diagram showing an illustrative process for identifying variations in the synthesis of polymers using physically detectable tags.

FIG. 1 shows process 100 for real-time detection of errors in polymer synthesis. Process 100 encompasses each of the specific techniques shown in FIGS. 2-6. Although many of the example implementations discuss oligonucleotide synthesis, the techniques of this disclosure are not limited to oligonucleotides. Synthesis of other polymers such as, but not limited to, polypeptides may also be observed in real-time by use of physically detectable tags.

Oligonucleotides, also referred to as polynucleotides, include both deoxyribonucleic acid (DNA), ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases.

At operation 102, physically detectable tags 104 are incorporated during the synthesis of polymers 106. The specific way in which physically detectable tags 104 are incorporated during polymer synthesis may vary with the type of physically detectable tag 104, the type of polymer 106, and the synthetic technique. In some implementations, the physically detectable tags 104 are or include fluorophores. Other types of physically detectable tags 104 may also be used including, but not limited to, redox probes. In one implementation, the physically detectable tags 104 are associated with nucleotide triphosphates which are added to the end of growing oligonucleotide strands.

The polymers 106 are synthesized on addressable array 108. The polymers 106 are synthesized using a solid-phase synthesis technique in which the growing polymer strands are attached to a substrate and not free to move about in solution. Techniques for solid-phase synthesis of polymers such as oligonucleotides and polynucleotides are known to those of skill in the art.

Solid-phase synthesis of oligonucleotides may be performed enzymatically with substrate independent polymerases. Substrate independent polymerases are DNA or RNA polymerases that perform de novo oligonucleotide synthesis without use of a template strand. Currently known substrate independent polymerases include TdT and tRNA nucleotidyltransferase. TdT includes both the full-length wild-type enzyme, as well as modified enzymes that are truncated or internally modified. TdT adds nucleotides indiscriminately to the 3' hydroxyl group at the 3' end of single-stranded DNA. TdT performs unregulated synthesis adding any available dNTP.

Because TdT performs unregulated synthesis, using this enzyme to create a polynucleotide with a pre-specified arbitrary sequence requires regulation and control of the TdT activity. One technique to regulate TdT activity is limiting the available nucleotides to only a single type of dNTP or NTP (e.g., only dATP, dCTP, dGTP, dTTP, or UTP). Thus, providing only one choice forces the enzyme to add that type of nucleotide. However, this does not prevent the TdT from adding that nucleotide multiple times thereby creating homopolymers. Techniques for limiting homopolymer creation by TdT include using nucleotides with removable protecting groups or covalently coupling individual nucleotides to TdT enzymes so that the enzyme acts as a blocking group.

One technique for controlling enzymatic synthesis of oligonucleotides with TdT uses a modified TdT enzyme and dNTP analogs with protecting groups to prevent unregulated nucleotide addition. An example of this technique is described in U.S. Pat. No. 10,059,929. Techniques for enzymatic polynucleotide synthesis that use protecting groups typically flood a reaction tube with only one type of dNTP. The protecting group prevents polymerization so only a single nucleotide is added to the growing polynucleotide strand. Once coupling has taken place, the free dNTPs are washed away, the protecting group is removed with a deblocking solution, and the system is primed for the next round of single-nucleotide addition.

Another technique for enzymatic synthesis uses TdT enzymes each tethered to a single dNTP by a cleavable linker. See Sebastian Palluck et al., De novo *DNA synthesis using polymerase-nucleotide conjugates,* 36(7) Nature Biotechnology 645 (2018) and WO 2017/223517 A1. In this system, the TdT acts as its own protecting group preventing further chain elongation.

Solid-phase synthesis of peptides (SPPS) is a well-known technique for synthesizing polymer strands. SPPS allows the rapid assembly of a peptide chain through successive reactions of amino acid derivatives on an insoluble porous substrate. The general SPPS procedure is one of repeated cycles of alternate N-terminal deprotection and coupling reactions. The cycles are repeated until the desired sequence has been synthesized. SPPS cycles may also include capping steps that block the ends of unreacted amino acids from reacting.

The addressable array 108 may be implemented as any solid substrate on which polymers 106 can be grown. In some implementations, the addressable array 108 may be an inert surface such as silicon dioxide or glass. The addressable array 108 may also be implemented as a microelectrode array.

The microelectrode array may contain a large number of microelectrodes that make it possible to create many different oligonucleotides (e.g., 10,000, 60,000, 90,000, or more) on the surface of a single array. This high level of multiplexing is made possible in part by the microelectrode density which may be approximately 1000 microelectrodes/$cm^2$, 10,000 microelectrodes/$cm^2$, or a different density. Examples of suitable microelectrode arrays are provided in Bo Bi et al., *Building Addressable Libraries: The Use of "Safety-Catch" Linkers on Microelectrode Arrays,* 132 J. Am. Chem. Soc. 17,405 (2010) and in U.S. Pat. Pub. No. 2020/0384434 filed on Jun. 7, 2019, with the title "Reversing Bias in Polymer Synthesis Electrode Array." One example of a microelectrode array and techniques for attaching polynucleotides to the surface of the array is provided in Ryan D. Egeland & Edwin M. Southern, *Electrochemically Directed Synthesis of Oligonucleotides for DNA Microarray Fabrication,* 33(14) Nucleic Acids Res. e125 (2005).

Other techniques for providing spatial control polymer growth on the surface of an addressable array 108 include the use of directed application of light such as through a photomask by digital micromirror and controlled application of chemical reagents to the surface of the addressable array 108 such as by chemical inkjet printing. Multiple techniques for providing spatial control of oligonucleotide synthesis on the surface of an addressable array 108 are known to those of ordinary skill in the art. Some illustrative techniques are described in U.S. Pat. Pub. No. 2021/0071170 with the title "Array-Based Enzymatic Oligonucleotide Synthesis" filed on Sep. 9, 2019. Any technique that provides spatial control of polymer 106 synthesis on the surface of addressable array 108 may be used with the content of this disclosure. Each of these techniques allows for the creation of a population of polymers 106 with different sequences.

The surface of the addressable array 108 has multiple individually addressable locations at which polymer synthesis may be separately controlled. These locations are referred to herein as "spots" 108. All polymers 106 synthesized at the same spot 110 will have the same sequence. However, polymers 106 synthesized at a different spot 110 may have a different sequence. If the addressable array 108 is implemented as a microelectrode array, a spot 110 may represent a single microelectrode of the microelectrode array. The size of a single spot 110 can be smaller than about 1 cm$^2$, smaller than 1 mm$^2$, smaller than 0.5 mm$^2$, and in some implementations about 0.125 to 0.5 mm$^2$.

Each spot 110 is individually addressable either by activating a microelectrode or other technique and has a known location on the surface of the addressable array 108. In an implementation, the spots 110 may be arranged in a grid pattern. However, other arrangements are also possible. The addressable array 108 illustrated in FIG. 1 includes only four spots 110, but in a typical implementation an addressable array 108 will contain many hundreds, thousands, or hundreds of thousands of spots 110. The spots 110 in the illustrated addressable array 108 may be identified by column and row labels such as A1, B1, A2, and B2. Any other labeling identification technique may also be used. Thus, each portion on the surface of the addressable array 108 which may be separately controlled in order to create polymers 106 having a unique sequence has a known and identifiable location.

Synthesis of the polymers 106 proceeds according to the specific technique for sequential polymer subunit 112 addition. For the synthesis of oligonucleotides, the polymer subunits 112 are nucleotides or deoxyribonucleotides. For the synthesis of polypeptides, the polymer subunits 112 are amino acids. Other types of polymer subunits 112 are also possible such as combinations of multiple nucleotides, double-stranded oligonucleotide structures, or combinations of multiple amino acids.

During synthesis of the polymers 106, physically detectable tags 104 are incorporated either into the growing polymer itself, as a blocking group on a polymer subunit 112, as a blocking group used elsewhere, any template strand or other location that is not part of the polymer 106 itself, and the like. The specific way in which the physically detectable tag 104 is incorporated during synthesis of the polymers 106 will vary with the particular technique used for polymer synthesis. In any implementation, detection or loss of detection of the physically detectable tag 104 indicates the formation of a covalent bond such as addition of a polymer subunit 112 or non-covalent binding such as hybridization of single-stranded oligonucleotides. Thus, the physically detectable tags 104 enable real-time observation of one or more aspects of the chemistry occurring during polymer synthesis.

Fluorophores are one type of physically detectable tag 104 commonly used in biotechnology applications. Examples of fluorophores include small-molecule dyes, green fluorescent protein, Alexa Fluor 647—AF647, Cy5, DyLight 488, Fluorescein-12-ddUTP, Cy™3-ddUTP, Cy5-UTP, and Cy3-UTP, Cy3, Cy5, CR-6G, 6-FAM, HEX, TAMRA, and TET. However, physically detectable tags 104 in this disclosure are not limited to fluorophores and may include other types of tags that can be sensed or detected by appropriate instrumentation.

In an implementation, the physically detectable tags 104 may be redox probes detected through direct redox behavior or changes in a catalytic current cycle of a reporter. Techniques for using redox probes in DNA sensors are known in the art. One type of redox probe is a ferrocene moiety. Use of ferrocene redox labels to detect real-time hybridization of DNA on CMOS chips is described in Levine et al., Real-time, multiplexed electrochemical DNA detection using an active complementary metal-oxide-semiconductor biosensor array with integrated sensor electronics, *Biosens Bioelectron.* 2009 Mar. 15; 24(7): 1995-2001. Another type of redox probe is tethered methylene blue. See Lubin et al., Effects of Probe Length, Probe Geometry, and Redox-Tag Placement on the Performance of the Electrochemical E-DNA Sensor, *Anal. Chem.,* 2009, 81, 6, 2150-2158.

Redox probes may be detected via voltammetry. In voltammetry, information about an analyte is obtained by measuring the current as the potential is varied. The analytical data for a voltammetric experiment comes in the form of a voltammogram which plots the current produced by the analyte versus the potential of the working electrode. Electrochemical DNA sensors measure electronic activity that results from the hybridization of ssDNA targets to probes immobilized on metallic or carbon working electrodes immersed in an electrolyte. The nature of this electronic activity depends on the sensing methodology used but often involves the introduction of electrochemically active labels on the target DNA. A potentiostat applies a desired input voltage to the electrochemical cell and measures the resulting current passing through the working electrode. The individual electrodes in a microelectrode array may be working electrodes.

At operation 114 following incorporation of the physically detectable tags 104, the physically detectable tags 104 are detected at a plurality of locations on addressable array 108. The physically detectable tags 104 are detected by a detection device that may generate detection data. The specific type of detection device will vary with the type of physically detectable tag 104. For example, fluorophores may be detected by fluorescent microscopy. In which case that section data would be an image captured by a fluorescent microscope. The image may be a color image that captures differences in the colors emitted by different types of fluorophores. Alternatively, the image may be monochromatic in which only intensity of fluorescence is detected. Techniques for detecting fluorophores associated with oligonucleotides are known to those of ordinary skill in the art and include techniques used for analysis of microarrays and observation of single nucleotide binding in sequencing-by-synthesis techniques for oligonucleotide sequencing. Techniques for detecting redox probes include voltammetry. The detection data for voltammetry may be a voltammogram.

Detection of the physically detectable tags 104 may create a captured representation 116 of the surface of the addressable array 108. The captured representation 116 may be an image captured by fluorescent microscopy or a voltammogram captured by voltammetry. The captured representation 116 represents the state of the addressable array 108 during a point in polymer synthesis and shows the locations where the physically detectable tags 104 are either detected or not detected. The presence or absence of the physically detectable tags 104 at specific locations on the addressable array 108 indicates the formation of covalent bonds or non-covalent binding.

At operation 118, the plurality of locations where the physically detectable tags 104 are detected and compared to preexisting data indicating locations of expected fluorescence on the addressable array. The expected locations 120 are determined based on both the sequence of the polymers 106 that will be synthesized and the individual spots 110 on the surface of the addressable array 108 at which each particular polymer sequence is to be created. Knowledge of polymer sequences to be synthesized at individual spots 110 on the surface of the addressable array 108 is used to create expected locations 120 of tag detection during each step of polymer synthesis. Expected locations 120 may be represented as a map or diagram of the surface of the addressable array 108 that contains values for individual locations on the addressable array 108. The values may be colors, wavelengths of light, electrical voltages, or the like. For example, the expected locations 120 may indicate that spot A2 on the addressable array 108 is expected to fluoresce at a wavelength of about 700 nm.

Imaging or other technique for detection of the physically detectable tags 104 may be repeated every round of synthesis or may be performed less frequently. For example, detection of the physically detectable tags 104 may be performed only every other round, every tenth round, or at a different frequency. It may not be possible to identify the sequence of the polymer 106 if detection is performed only intermittently, but intermittent detection can be used to identify the prevalence of errors.

A captured representation 116 showing where the physically detectable tags 104 are detected may be compared to the expected locations 120 of tag detection. This comparison may be performed for the entire surface of the addressable array 108 or for only a subset of the addressable array 108. Similarly, the comparison may be performed for all or less than all of the spots 110 on the addressable array 108. For example, a fluorescent microscopy image showing red fluorescence at spot A1 on addressable array 108 may be compared to data indicating that fluorescence of about 700 nm expected at spot A1 at this cycle of synthesis. The presence of a variation 122 between the captured representation 116 and the expected locations 120 may indicate an error in synthesis. Thus, it may be determined for each of the individual ones of the plurality of locations on the addressable array 108 if the captured representation 116 matches the corresponding value expected at that location. This makes it possible to perform quality control across the entire addressable array 108 and at each individual spot 110.

At operation 124, it is determined if a variation 122 is found. This determination may be made for all or less than all of the spots 110 on the addressable array 108. If no variation is found, meaning that the captured representation 116 matches the expected locations 120 of observable physically detectable tags 104, then process 100 may return to operation 102 and repeat for addition of a subsequent polymer subunit 112. This process may be repeated until the polymers 106 are fully synthesized. Following synthesis, the polymers 106 may be cleaved from the surface of the addressable array 108 using techniques known to those of ordinary skill in the art for solid-phase synthesis.

If a variation is found, some type of mitigating action may be taken at operation 126. The ability to identify variations during synthesis makes it possible to mitigate synthesis of polymers in real-time which is not possible if quality control can only be performed after synthesis is fully complete.

Possible mitigating actions include discarding the polymers, modifying synthesis of the polymers, or saving data 128 that describes the variation.

The mitigation may be disposal of the partially synthesized polymers and abandonment of the synthesis run. Stopping the synthesis of a plurality of polymers may be the mitigating action taken if there are frequent errors or errors indicating some type of systemic problem with the synthesis system. Discarding the polymers 106 before synthesis is complete avoids wasting reagents to finish the synthesis of polymers that will ultimately be unusable. Additionally, this allows the equipment to be made available for synthesizing a subsequent batch of polymers.

Modifying synthesis of the plurality of polymers allows for correction or mitigation of any detected errors. If the variation 122 indicates that a polymer subunit 112 which was expected to be added to a growing polymer 106 was not attached, synthesis may be modified by recontacting the addressable array 108 with the species of polymer subunit 112 that was previously added. If the variation 122 indicates that removal of a blocking group was not successful, synthesis may be modified so that the deblocking step is repeated. Other types of specific modifications will depend on the particular synthetic technique and the chemical reaction represented by the physically detectable tag 104. Generally, if the variation 122 indicates that a step of synthesis was not completed successfully, that step may be repeated as a mitigating action. Because each of the spots 110 on the addressable array 108 are individually addressable, repeating of a step or modification of synthesis may be performed only to those spots 110 at which a variation 122 was detected.

A third type of mitigation is the creation and saving of data 128 that describes the variation 122. The data 128 may be electronic data such as a computer file. This data 128 may be metadata that describes the characteristics of a collection of polymers 108 created in a synthesis run. If the polymers are used for encoding digital data such as a computer file, the metadata may also include a file name of the encoded computer file. In some implementations, the data 128 may be associated with an indication of a physical container 130 in which the polymers 108 are stored such as a dried spot on filter paper, a tube, or location in a well. For example, data 128 containing descriptions of some or all of the variations 122 detected during the synthesis of a plurality of polymers 108 may include or be linked to a unique identifier (e.g., tube number) of a container that holds the polymers 108. Thus, the data 128 may describe the accuracy of the polymer synthesis. For example, the data 128 describing the variation 122 may include data indicating locations of deblocking and data indicating locations of polymer subunit 112 addition.

In some implementations, process 100 may further comprise a step of calculating synthesis yield for the plurality of polymers from the data 128. The synthesis yield may be calculated for each spot 110 on the addressable array 108. The synthesis yield of a given step at a given spot 110 may be calculated by comparing the intensity of the signal in captured representation 116 originating from physically detectable tag 104 to a calibration curve. A suitable calibration curve may be generated from signal intensity data paired with known synthesis yield by statistical modelling. An overall synthesis yield for the entire synthesis process at a given spot 110 may be calculated by composition of all calculated yields for independent synthesis steps. Synthesis bias derived from the yield may be added to the data 128.

In some implementations, the synthesis yield may be calculated by calibrating a fluorescence intensity to base addition. Max fluorescence is normalized to 100% of the coupling efficiency and zero/background fluorescence is set to 0% coupling efficiency. For example, if average coupling efficiency is 99%, an oligonucleotide of 30 bases would have about $0.99\hat{}30=\sim74\%$ synthesis yield of full-length product. Thus, the fluorescence intensity generated by 74% yield would be the max fluorescence. If the physically detectable tag is a redox probe, the coupling efficiency could be normalized to magnitude of the current delta.

De novo synthesis of a plurality of polymers 106 may repeat many rounds or cycles of adding polymer subunits 112 to the growing polymers 106. Each of the steps of process 100 may be repeated until synthesis of the plurality of polymers is complete. Thus, whenever a variation is found at operation 124, there may a modification of the polymer synthesis (either across the entire addressable array 108 or only at the spots 110 where the variation was detected). Additionally or alternatively, the data 128 may be changed by cumulative addition of descriptions of any variations detected during each round of synthesis.

Figure 2:
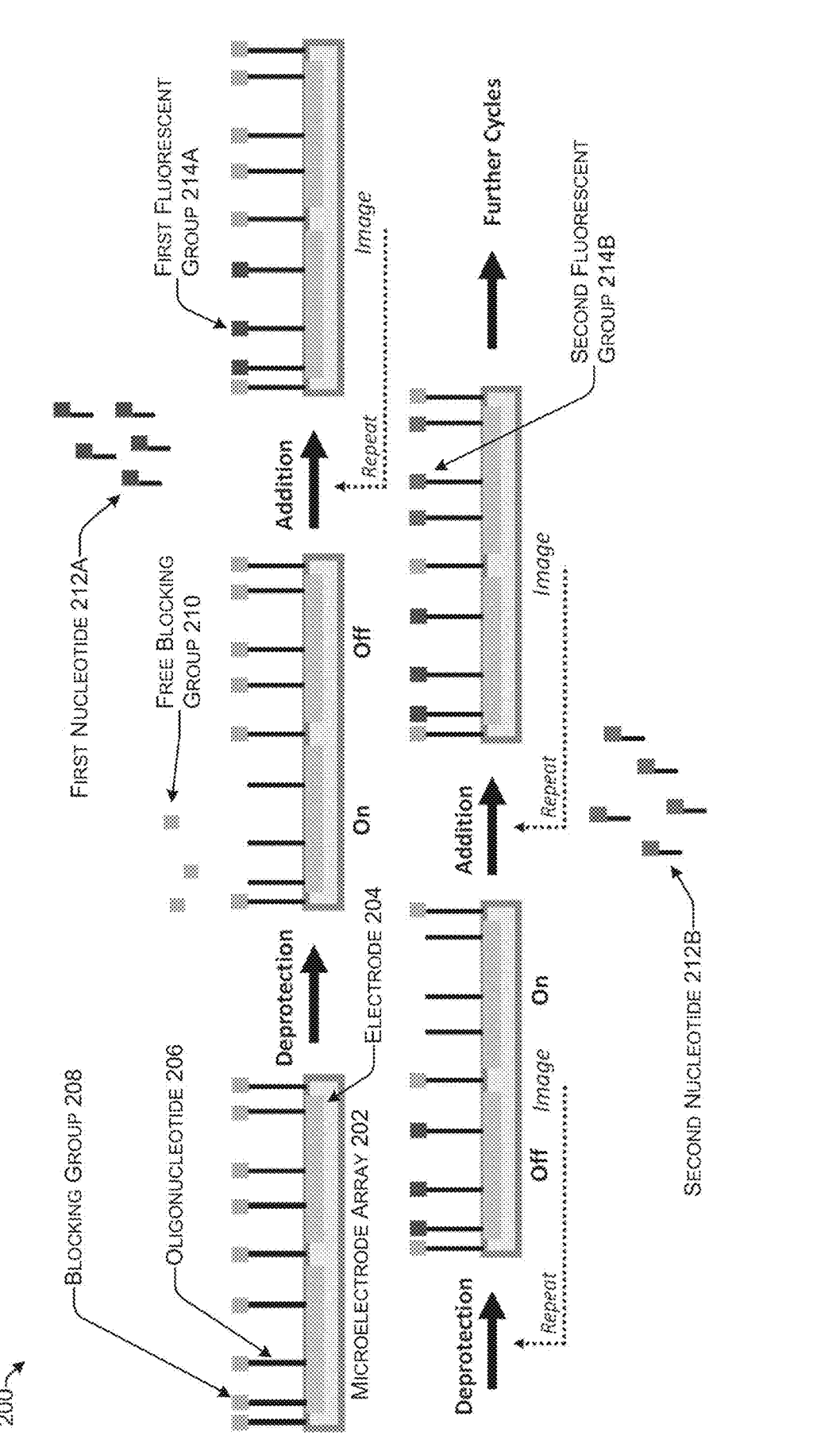
FIG. 2 illustrates an implementation of the techniques of this disclosure for monitoring incorporation of fluorescently labeled nucleotides in non-templated, enzymatic synthesis of oligonucleotides.

FIG. 2 shows a schematic diagram 200 of one example implementation in which a microelectrode array 202 having multiple electrodes 204 is used to synthesize oligonucleotides 206 by non-templated, enzymatic synthesis. Techniques for non-templated enzymatic synthesis of oligonucleotides using terminal deoxynucleotidyl transferase (TdT) or a similar enzyme are known to those of skill in the art and described in U.S. Pat. No. 10,059,929, Palluck et al. supra, and WO 2017/223517 A1. Example techniques for solid-phase enzymatic synthesis of oligonucleotides using TdT with removable blocking groups on nucleotides are described in U.S. 2021/0071170.

Oligonucleotides 206 are attached to the surface of the microelectrode array 202. Multiple oligonucleotides 206 may be attached to the same electrode 204. The electrodes 204 correspond to the spots 110 of FIG. 1. Techniques for attaching oligonucleotide strands to the surface of a substrate such as a microelectrode array 202 are known to those of ordinary skill in the art. Examples include silane functionalization which covers a surface with organofunctional alkoxysilane molecules or agarose functionalization which covers a surface with a polysaccharide matrix. Examples of linkers that may be used are provided in U.S. Pat. Publication No. 2020/0199662 filed on Dec. 21, 2018, with the title "Selectively Controllable Cleavable Linkers." Non-covalent attachment such as streptavidin-biotin interactions may also be used to attach the anchor oligonucleotides to the surface of an addressable array. Techniques for attaching other polymers such as polypeptides are also known to those of ordinary skill in the art.

With this synthetic technique, a growing single-stranded oligonucleotide 206 is immobilized on the surface of the microelectrode array 202. The 3' terminus of the growing oligonucleotide 206 is initially capped with a blocking group 208 that inhibits enzymatic addition of additional nucleotides to the 3' terminus. The initial blocking group 206 may be a non-fluorescent blocking group. However, in some implementations, the blocking 208 group may be associated with a fluorescent tag or another type of physically detectable tag.

Some examples of blocking groups include esters, ethers, carbonitriles, phosphates, carbonates, carbamates, hydroxylamine, borates, nitrates, sugars, phosphoramide, phosphoramidates, phenylsulfenates, sulfates, sulfones, and amino acids. See Michael L. Metzker et al., *Termination of DNA Synthesis by Novel* 3'-*modified-deoxyribonucleoside* 5'-*triphosphates*, 22(20) Nucl. Acids Res., 4259 (1994) and U.S.

Pat. Nos. 5,763,594, 6,232,465, 7,414,116, and 7,279,563. Other types of blocking groups include 3'-O-amino, 3'-O-allyl, and a 3'-O-azidomethyl groups. Examples of blocking groups also include O-phenoxyacetyl; O-methoxyacetyl; O-acetyl; O-(p-toluene)-sulfonate; O-phosphate; O-nitrate; O-[4-methoxy]-tetrahydrothiopyranyl; O-tetrahydrothiopyranyl; O-[5-methyl]-tetra-hydrofuranyl; O-[2-methyl,4-methoxy]-tetrahydropyranyl; O-[5-methyl]-tetrahydropyranyl; and O-tetrahydrothiofuranyl. See U.S. Pat. No. 8,133,669 for a discussion of these blocking groups.

To begin a synthesis cycle, the blocking group 208 is removed from a spatially isolated subset of the growing oligonucleotides 206 by activation of one or more of the electrodes 204. This results in free blocking groups 210 in solution. The free blocking groups 210 may be removed by a wash step. This and all washing steps in this disclosure may be performed with water or an aqueous wash buffer. Specific techniques for removing a blocking group by activation of electrodes 204 are described in U.S. 2021/0071170.

Next, a first nucleotide 212A is added to the deblocked growing oligonucleotides 206 by action of TdT or a similar enzyme. Generally, a single species of nucleotide is added thereby controlling which nucleotide base is incorporated into the growing oligonucleotides 206. However, in some implementations more than one species of nucleotide may be added at the same time. This can create a stochastic distribution of nucleotides at a given position in a population of synthesized oligonucleotides 206. The first nucleotide 212A includes or is attached to a first fluorescent blocking group 214A.

After addition, the surface of the microelectrode array 202 may be imaged after addition of the nucleotide with the first fluorescent group 214A. This imaging may be performed by any suitable technique such as fluorescent microscopy or other techniques such as those used for imaging DNA microarrays. The locations of nucleotides 212 and associated fluorescent groups 214 may be measured with a scanner consisting of one or more sources for excitation and a photomultiplier tube or charge-coupled device camera to detect the emitted light. This imaging creates a captured representation as discussed in FIG. 1.

Relative expression levels of bound targets at different array sites can then be quantified from the resulting image. If a variation is detected, namely if fluorescence is not detected where expected on the surface of the microelectrode array 202, the addition step may be repeated by recontacting the surface of the microelectrode array 202 with the first nucleotides 212A that was previously added. Thus, detecting the physically detectable tags at a plurality of locations on an addressable array comprises detecting fluorescence at a subset of the addressable electrodes 204, the fluorescence indicating successful incorporation of the first nucleotides 212A.

Synthesis of the oligonucleotides 206 proceeds with additional cycles of deprotection and addition of nucleotides 212. The schematic diagram 200 shows addition of a second nucleotide 212B with a second fluorescent group 214B. However, in typical implementations the cycles of deprotection and nucleotide addition will be repeated multiple times. Imaging may be performed at each deprotection step and after each addition step. In this example, fluorescent groups 214A and 214B fluoresce at different wavelengths. In some implementations, each species of nucleotide may be associated with a different fluorescent group that fluoresces in a different color. For example, if a plurality of oligonucleotides is synthesized from four different species of nucleotide, each species of nucleotide may fluoresce with a different color. (e.g., A=red, G=green, C=yellow, T=blue). This makes enables true sequencing during synthesis not just confirmation of nucleotide addition. However, in other implementations all species of nucleotides may be associated with the same fluorescent group. If the same fluorescent group is used for all nucleotide species, nucleotide addition can be detected but it is not possible to determine by fluorescence if an incorrect nucleotide species is added.

Imaging of the deprotection steps will show a loss of fluorescence when the blocking groups are successfully removed. Thus, detecting the physically detectable tags at a plurality of locations on an addressable array may include detecting a loss of fluorescence at a subset of the addressable electrodes 204, the loss of fluorescence indicating removal of a blocking group. If there is a variation in the locations of loss of fluorescence compared to expected locations, the deblocking may be repeated by selectively reactivating the electrodes 204 where loss of fluorescence was expected but not observed.

There are many possible ways a fluorescent group 214 can be associated with a nucleotide 212. In one implementation of enzymatic oligonucleotide synthesis, individual nucleotides are directly conjugated to TdT such that the enzyme acts as a blocking group preventing addition of more than one nucleotide at a time. This technique for controlling single nucleotide addition in the enzymatic synthesis of oligonucleotides 206 is described in Palluck et al. supra and WO 2017/223517 A1.

In one implementation, the fluorescent group 214 may be a small molecule dye conjugated via a linker moiety to the nucleotide or to the enzyme. The functioning of small molecule dyes is explained and examples are provided in Yanhua Fua and Nathaniel S. Finney, Small-molecule fluorescent probes and their design, RSC Adv., 2018, 8, 29051-29061. Examples of small molecule dyes include Alexa Fluor 647, Cy5, and DyLight 488. Examples of linkers used to attach dyes to nucleotides are provided in Fei Chen, et. al., The History and Advances of Reversible Terminators Used in New Generations of Sequencing Technology, 11 Genomics Proteomics Bioinformatics 34-40 (2013). A small molecule dye may also be conjugated to the nucleotide base. Techniques for conjugating dyes to nucleotide bases are known to those of ordinary skill in the art. For example, 3' end labeling of microarrays with fluorescently labeled dideoxynucleotides or ribonucleotides is discussed in Cesar E. Guerra, Analysis of oligonucleotide microarrays by 3' end labeling using fluorescent nucleotides (fluorescein-12-ddUTP, Cy3-ddUTP, Cy5-UTP, and Cy3-UTP) and terminal transferase, BioTechniques, Volume 41, Number 1, 2006.

In one implementation, the fluorescent group 214 is formed from a fusion protein of the polymerase (e.g., TdT) and a fluorescent protein such as green fluorescent protein (GFP). Techniques for making fusion proteins are known to those of ordinary skill in the art. For example, a method of making N-terminal GST-tagged fusion proteins is described in Thai and Kearney, The Journal of Immunology, Sep. 15, 2004, 173 (6) 4009-4019.

In one implementation, a fluorescently labeled antibody the recognizes the polymerase-linker-nucleotide complex or a portion thereof may be used as the fluorescent group 214. Examples of suitable fluorescent labels for antibodies include succinimidyl esters, maleimides, pyridyl disulfides, and fluorescent Fc-binding antibodies. Antibodies known to bind to TdT are commercially available including purified anti-TdT Antibody available from BioLegend of San Diego, California, USA. Fluorescently labeled antibodies may also recognize a nucleotide with a blocking group. Drmanac et al., CoolMPS™: Advanced massively parallel sequencing using antibodies specific to each natural nucleobase, bioRxiv 2020.02.19.953307 describes use of base-specific 3' block-dependent fluorescently labeled antibodies to fluorescently label nucleotides.

In one implementation, a "click chemistry" handle may be used to attach a small molecule dye to the nucleotide 212 or to the linked polymerase. Winz et al., Nucleotidyl transferase assisted DNA labeling with different click chemistries, Nucleic Acids Research, Volume 43, Issue 17, 30 Sep. 2015, Page e110, shows techniques for attaching different fluorophores Alexa Fluor 647—AF647, Cy5, or DyLight 488) to nucleotides using click chemistry type reactions, namely copper-catalyzed azide-alkyne cydoaddition, strain-promoted azide-alkyne cycloaddition, Staudinger ligation or Diels-Alder reaction with inverse electron demand.

It is also possible that the fluorescent group 214 is not physically associated, or even close to, the blocking group so long as both are removed under the same conditions. For example, if the blocking group and the fluorescent group 214 are both cleaved by the same or similar redox conditions, activation of an electrode that creates redox conditions to remove the blocking group will also release the fluorescent group 214. If the polymer subunit is a nucleotide triphosphate, a 3'-blocking group can block addition of subsequent nucleotides while a fluorophore-modified base provides the fluorescent group 214. For example, the 3'-azidomethyl blocking group and an azide-based cleavable linker may be cleaved in a single step by reduction. Both would be separated from the nucleotide when an electrode is activated and removed from the surface of the microelectrode array 202 by washing. As an additional example, the fluorescent group 214 (e.g., nitrobenzyl group) may be attached via a linker molecule to a non-fluorescent blocking group.

Figure 3:
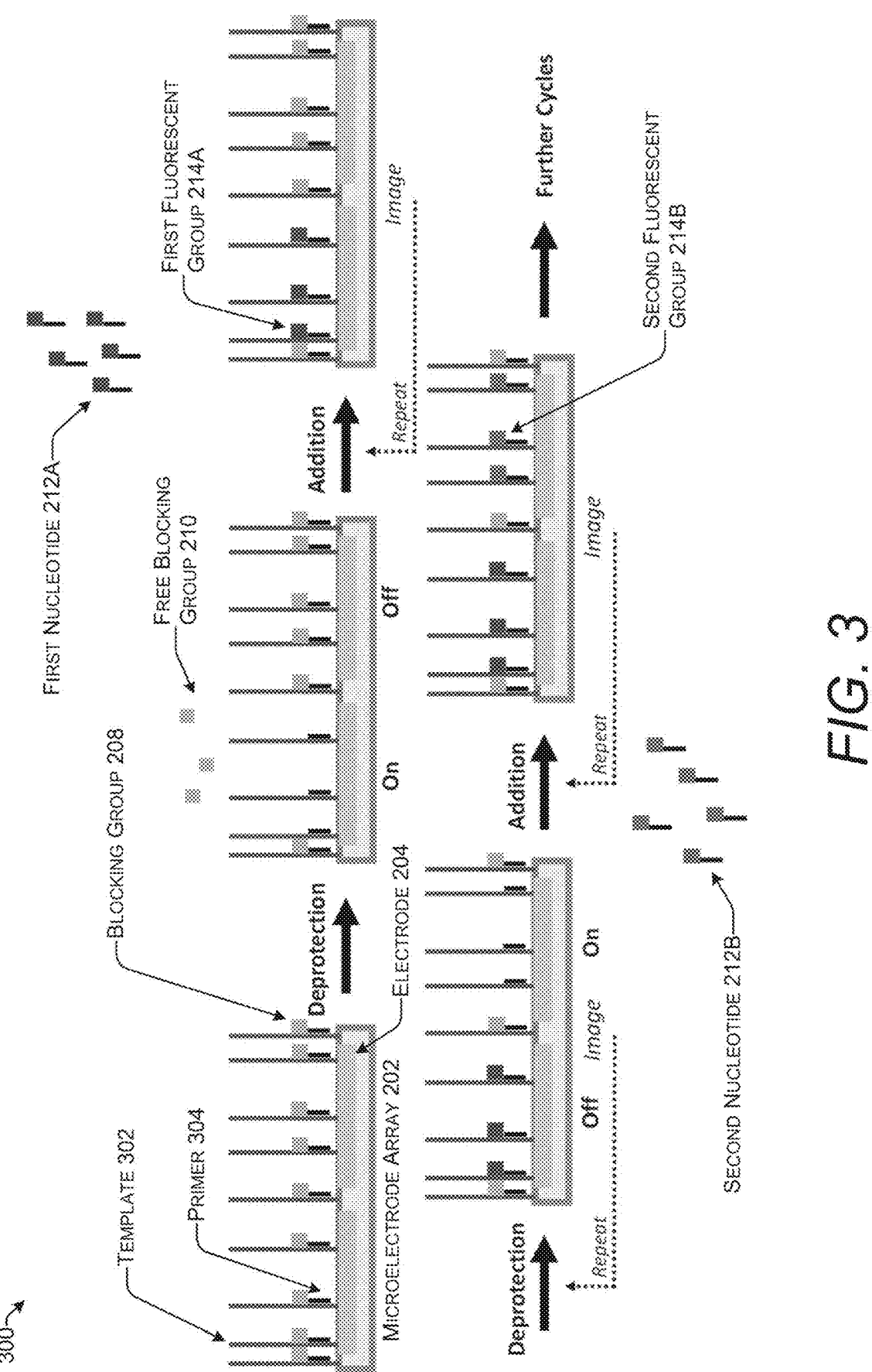
FIG. 3 illustrates an implementation of the techniques of this disclosure for monitoring incorporation of fluorescently labeled nucleotides in templated, enzymatic synthesis of oligonucleotides.

FIG. 3 shows a schematic diagram 300 of one example implementation in which a microelectrode array 202 having multiple electrodes 204 is used to synthesize oligonucleotides 206 by templated, enzymatic synthesis. Templated, enzymatic synthesis is a variation of enzymatic oligonucleotide synthesis that uses a universal template strand or simply template 302 to create a double-stranded structure with the oligonucleotide 206 having a specified sequence. The template 302 includes universal base analogs that pair with any of the natural nucleotide bases. Use of a template 302 increases the types of polymerases that may be used because unlike TdT, some polymerases, such as DNA-dependent DNA polymerases, require a double-stranded molecule to incorporate nucleotides. Details of a technique for templated, enzymatic synthesis are provided in U.S. patent application Ser. No. 16/865,262 titled "Universal Template Strands for Enzymatic Polynucleotide Synthesis," and filed on May 1, 2020.

The templates 302 are immobilized on the surface of a microelectrode array 202 through functionalization or by a linker. Many linkers and other techniques for attaching oligonucleotides to the surface of a substrate are known to those of ordinary skill in the art. Examples include silane functionalization which covers a surface with organofunctional alkoxysilane molecules or agarose functionalization which covers a surface with a polysaccharide matrix. Non-covalent attachment such as streptavidin-biotin interactions may also be used to attach the templates 302 to the microelectrode array 202.

Imaging of de novo oligonucleotide synthesis using a template 302 is similar to that for non-templated, enzymatic synthesis described above. An oligonucleotide primer 304 is hybridized to a primer region of a template 302 close to the surface of the microelectrode array 202. The 3' terminus of the oligonucleotide primer is initially capped with a blocking group 208 that inhibits addition of nucleotides to the 3' terminus. Removal of a 3' blocking group replaces the blocking group with a 3' hydroxyl group.

Suitable blocking groups 208 and methods for removing the 3' blocking groups include, but are not limited to, the 3' blocking groups and methods described in U.S. Pat. No. 7,541,444 and Chen et al., The History and Advances of Reversible Terminators Used in New Generations of Sequencing Technology, *Genomics, Proteomics & Bioinformatics*, Volume 11, Issue 1, 2013. Pages 34-40 of Chen et al. provide examples of several 3'-blocking groups used in DNA sequencing.

Any of these 3' blocking groups may be combined with a fluorescent group 214 by conjugating a small molecule dye to a nucleotide base, using a fluorescently-labeled antibody that recognizes the blocking group (See Drmanac et al.), or by a click chemistry handle which conjugates a molecule dye in a second step (See Winz et al). Examples of small molecule dyes that can be conjugated to the base of a nucleic acid are provided in Larry Kricka and Poloa Fortina, Analytical Ancestry: "Firsts" in Fluorescent Labeling of Nucleosides, Nucleotides, and Nucleic Acids, *Clinical Chemistry*, Volume 55, Issue 4, 1 Apr. 2009, Pages 670-683.

The blocking groups 208 may be removed from an area on the microelectrode array 202 by activation of a subset of the electrodes 204. The free blocking groups 210 may be removed by a washing step.

Subsequent rounds of adding a first nucleotide 212A, imaging, deprotection, imaging, addition of a second nucleotide 212B, imaging, and further cycles are repeated as with non-templated enzymatic oligonucleotide synthesis.

Figure 4:
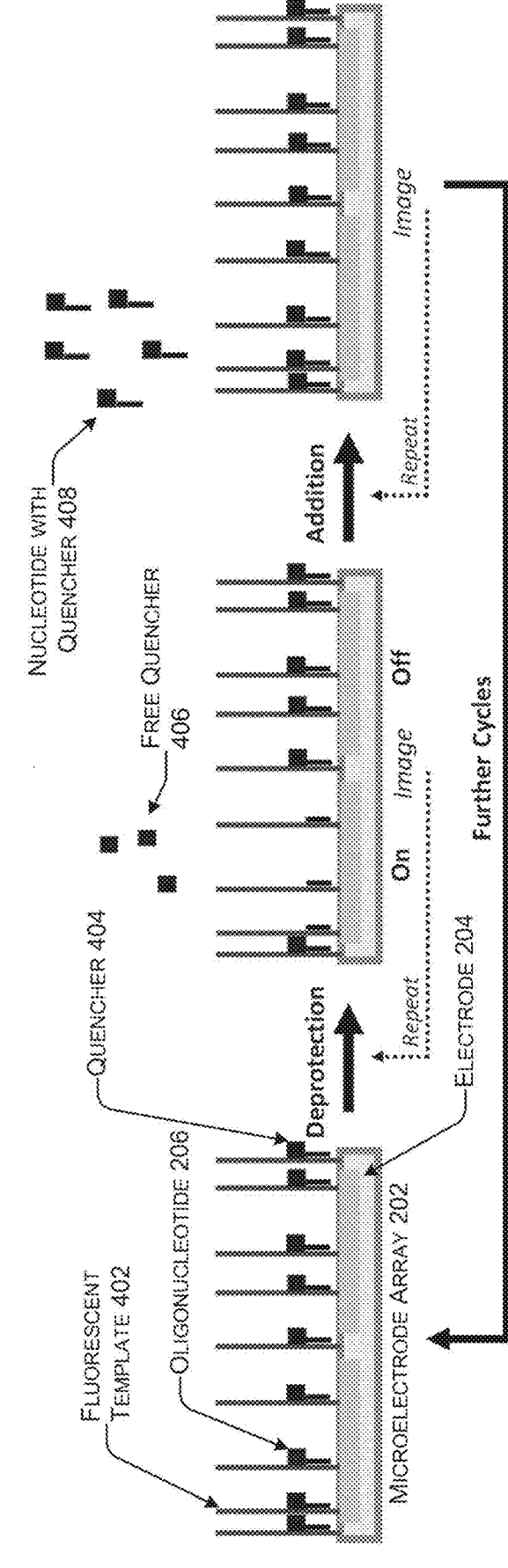
FIG. 4 illustrates an implementation of the techniques of this disclosure for monitoring templated, enzymatic synthesis of oligonucleotides in which the template strand contains fluorescent tags and individual nucleotides are associated with fluorescent quenchers.

FIG. 4 shows a schematic diagram 400 of one example implementation in which a microelectrode array 202 having multiple electrodes 204 is used to synthesize oligonucleotides 206 by templated, enzymatic synthesis with a fluorescent template 402. This example differs from that shown in FIG. 3 because a fluorescent template 402 is used to provide the physically detectable tags rather than individual nucleotides. Thus, quenchers 404 associated with nucleotides are used to observe the process of the polymerization instead of fluorescent blocking groups.

In this example, the universal template strand is a fluorescent template 402 that contains interspersed fluorescent groups, providing a background level of fluorescence on all regions of the microelectrode array 202 to which the fluorescent templates 402 are bound. Small molecule dyes may be conjugated with the bases of the fluorescent template 402 using techniques known to those of skill in the art, including those discussed above, for attaching a dye to a nucleotide. Kricka and Fortina provide examples of techniques for noncovalent binding (e.g., staining or intercalation) of a fluorescent dye to nucleic acids in order to create a background level of fluorescence. With noncovalent binding, the dyes are not specific to any particular nucleotide base. As discussed above, the fluorescent template 402 includes universal bases which are non-natural bases that may hybridize to any of the natural nucleotide bases. Examples of nucleotides having non-natural bases that fluoresce are provided in Hwang, G. T. Single-Labeled Oligonucleotides Showing Fluorescence Changes upon Hybridization with Target Nucleic Acids. *Molecules* 2018, 23, 124.

The 3'-blocking groups are associated with a quencher 404 using any of the techniques discussed above for associating a fluorescent group with a 3'-blocking group (e.g., attachment of a small molecule dye, fluorescent antibody, or click chemistry) to create quenching blocking groups. Fluorescent quenchers are known to those of ordinary skill in the art and generally provide fluorescent quenching for specific types of fluorophores. Examples of fluorophore-quencher pairs are provided in Monroy-Contreras and Vaca, Molecular Beacons: Powerful Tools for Imaging RNA in Living Cells, *Journal of Nucleic Acids*, vol. 2011, Article ID 741723, 15 pages, 2011.

The observed changes in fluorescence when using quenchers 404 are different than when using fluorescent groups associated with nucleotides. Activation of electrode 204 removes the blocking groups associated with the quenchers 404 from a region on the surface of the microelectrode array 202. The free quenchers 406 are removed by a washing step. Imaging after the deprotection step should observe a higher level of fluorescent at the locations on the microelectrode array 202 where the quenchers 404 were removed. If higher levels of fluorescence are not observed at the expected locations, deprotection may be repeated at those locations by reactivating the corresponding electrodes 204.

Addition of free nucleotides associated with quenchers 408 reintroduces quenchers 404 to the portions of the microelectrode array 202 that were deprotected. This results in a drop in fluorescent intensity indicating successful coupling of the nucleotide with quencher 408. If there is a variance in where the drop in fluorescent intensity is detected, the addition of the nucleotides with quenchers 408 may be repeated.

Figure 5:
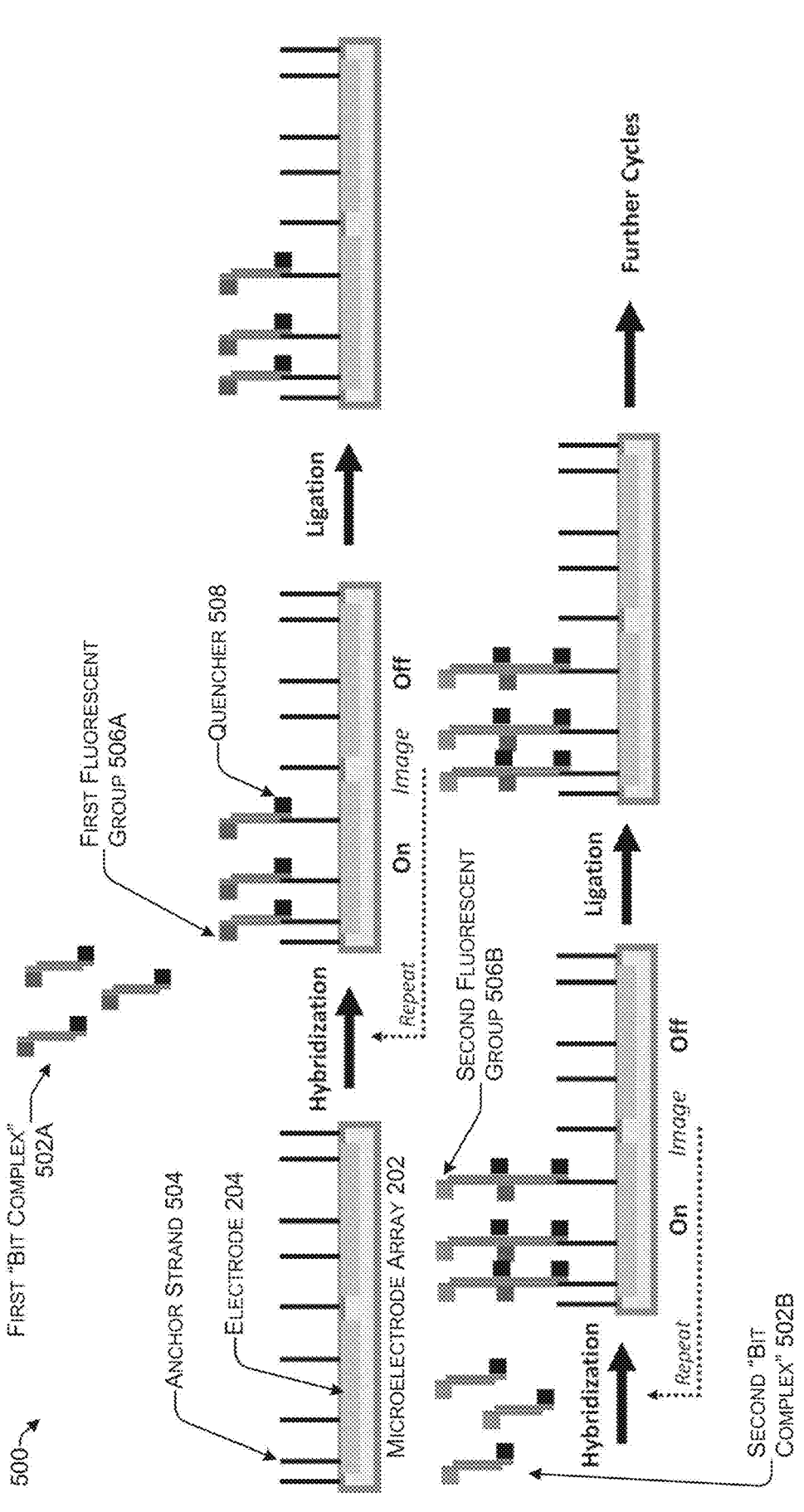
FIG. 5 illustrates an implementation of the techniques of this disclosure for monitoring ligation-based synthesis of oligonucleotide bit complexes that each include a fluorescent tag and a quencher.

FIG. 5 shows a schematic diagram 500 of oligonucleotides assembly by ligation of oligonucleotide "bit complexes" 502 labeled with a fluorescent group 506 and a quencher 508. Successive hybridization and ligation of bit complexes 502 to create a double-stranded oligonucleotide is a technique developed for encoding information in oligonucleotide sequences. This technique is described in U.S. patent application Ser. No. 16/698,860 with the title "Oligonucleotide Assembly Using Electrically Controlled Hybridization," filed on Nov. 27, 2019. This technique uses electrically controlled hybridization to selectively assemble oligonucleotides with specified, arbitrary sequences. These assembly techniques are alternatives to conventional phosphoramidite oligonucleotide synthesis and enzymatic oligonucleotide synthesis using TdT. The assembly techniques using bit complexes 502 are performed in an aqueous solution with common reagents. In this example, bit complexes 502 are a type of polymer subunit that is not just a single monomer unit (i.e., each bit complex 502 contains multiple nucleotides).

In brief, "bit complexes" 502 have a double-stranded payload region flanked by two single-stranded sticky ends or overhangs. The payload region may encode any arbitrary value such as a bit ("0" or "1"), a character (A, B, C, D, . . . ), or any other value. The bit complexes 502 initially hybridize to anchor strands 504 which are oligonucleotides attached to the surface of the microelectrode array 202. Oligonucleotides are negatively charged, thus the bit complexes 502 are attracted to electrodes 204 that generate a positive charge.

The microelectrode array 202 is coated with a plurality of anchor strands 504 by any of the techniques described herein for attaching oligonucleotides to a solid substrate. One of the sticky ends of the bit complexes 502 hybridizes to the anchor strand 504 attached to electrodes 204 generating a positive charge.

In order to provide stepwise monitoring of the process, the bit complexes include both fluorescent group 506 and the corresponding quencher 508 that quenches the fluorescence of the fluorescent group 506. In this example, a first fluorescent bit complex 502A includes a first fluorescent group 506A and a quencher 508 on opposite ends. When the first bit complex 502A hybridizes to the anchor strands 504, imaging of the microelectrode array 202 can detect the first fluorescent group 506A. If fluorescence is not detected at the locations expected, this may result in a variance and can be addressed by again adding the first bit complex 502A.

The first bit complexes 502A are hybridized to the anchor strands 504 then ligated by a ligase to seal the nick between one strand of the bit complex 502 and the anchor strand 504. There is no monitoring of the ligation step in this example. Ligases and suitable reaction conditions for performing ligation are known to those of ordinary skill in the art. One specific type of DNA ligase that is frequently used in molecular biology is T4 DNA Ligase isolated from bacteriophage T4.

Second bit complexes 502B are added. The second bit complexes 502B hybridize either to anchor strands 504 or two the first bit complexes 502A depending on which electrodes 204 are activated. In this example schematic diagram 500, the second bit complexes 502B hybridize to the first bit complexes 502A. Upon hybridization, the quencher 508 of bit complex 502B comes into proximity with the first fluorescent group 506A. The second fluorescent group 506B fluorescence at a different wavelength than the first fluorescent group 506A. Thus, a color change is indicative of successful hybridization. If the "bit complexes" 502 encode trits, for example, there may be more than three different fluorescent groups 506. Thus, each "bit complex" 502 that encodes a unique value may include a different fluorescent group 506 that fluoresces with a different color.

Structures somewhat similar to bit complexes 502—stem-loop hairpin-structured oligonucleotides equipped with a fluorescence quencher at one end and a fluorescent dye (also called reporter or fluorophore) at the opposite end—are described in Monroy-Contreras and Vaca, Molecular Beacons: Powerful Tools for Imaging RNA in Living Cells, *Journal of Nucleic Acids*, vol. 2011, Article ID 741723, 15 pages, 2011. In the example of FIG. 5, the fluorescent groups 506 are conjugated to nucleotide bases to allow for ligation rather than the 5' phosphate as described in Monroy-Contreras and Vaca. Suitable fluorescent groups 506 include Cy3, Cy5, CR-6G, 6-FAM, HEX, TAMRA, and TET. Suitable quenchers 508 include are Dabcyl (4-([4'-(dimethylamino)phenyl]azo)benzoic acid), Black-Hole quenchers BHQ1 and BHQ2, and Iowa Black FQ and RQ.

The microelectrode array 202 may again be imaged to detect the change in fluorescence. Change in fluorescence at expected locations on the surface of the microelectrode array 202 indicates successful hybridization of the second bit complex 502B to the first bit complex 502A. If there is a variation between where fluorescence is expected to change in where it is observed to change, the electrodes 204 at locations where the expected fluorescent change was not observed may be activated and the second bit complex 502B is again contacted with the microelectrode array 202. This process may be repeated multiple times extending the oligonucleotides by successive hybridization and ligation of bit complexes 502. Once synthesis is complete, the assembled double-stranded oligonucleotide is separated from the microelectrode array. All assembled double-stranded oligonucleotides attached to the surface of the microelectrode array may be separated in the same operation. Thus, in an implementation, separation of the double-stranded oligonucleotides is not selective. Following separation from the microelectrode array 202, the double-stranded oligonucleotide may be processed further such as, for example, by denaturation and amplification with PCR. The PCR product may be stored for short- or long-term.

Figure 6:
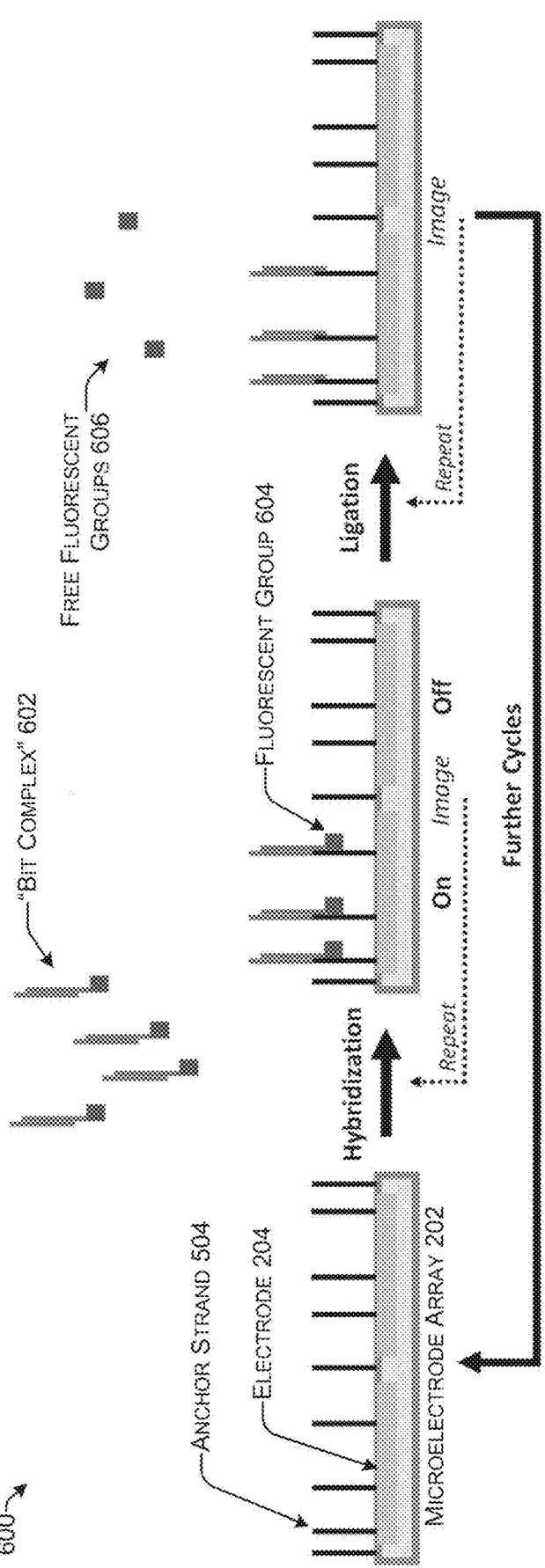
FIG. 6 illustrates an implementation of the techniques of this disclosure for monitoring ligation-based synthesis of oligonucleotide bit complexes that each include a fluorescently labeled terminal phosphate.

FIG. 6 shows a schematic diagram 600 of oligonucleotides assembly by ligation of "bit complexes" 502 labeled with a fluorescent group 506 attached to a terminal phosphate. This example differs from the example shown in FIG. 5 in that the nick closing action of ligase which is in addition to the hybridization of bit complexes 602. Other aspects of oligonucleotide assembly with bit complexes are the same.

In this example, the bit complexes 602 include a fluorescent group 604 on the terminal phosphate. Terminal phosphate-labeled nucleotides have been developed in pursuit of pyrosequencing and shown to be enzymatically compatible. Kumar et al., Terminal phosphate-labeled nucleotides have been developed in pursuit of pyrosequencing and shown to be enzymatically compatible, *Nucleotides, Nucleotides & Nucleic Acids*, volume 24, issue 5-7, 2005. Hybridization is detected by fluorescence allowing for confirmation that hybridization has occurred at expected locations on the surface of the microelectrode array 202. If there are locations on the microelectrode array 202 where hybridization, and thus fluorescence, was expected but is not observed, this variation may be mitigated by activating the electrodes 204 where expected fluorescence was not observed and reintroducing the bit complexes 602.

Ligation results in cleavage of the terminal phosphate, freeing the fluorescent group 604 from the bit complexes 602 attached to the surface of the microelectrode array 202. The free fluorescent group 606 may be removed with a wash step. Confirmation of ligation occurs via disappearance of fluorescence. If fluorescence does not disappear at locations where expected, ligase may be again added. This process is repeated over multiple cycles adding the same or different bit complexes 602 at specific locations on the surface of the microelectrode array 202 during each cycle until synthesis of the oligonucleotides is complete.

Unless otherwise specified, hybridization as used throughout this disclosure refers to the capacity for hybridization between two single-stranded oligonucleotides or oligonucleotide segments at 21° C. in 1×TAE buffer containing 40 mM TRIS base, 20 mM acetic acid, 1 mM ethylenediaminetetraacetic acid (EDTA), and 12.5 mM $MgCl_2$. Hybridization and washing conditions are well known and exemplified in Sambrook, J., Fritsch, E. F. and Maniatis, T. *Molecular Cloning: A Laboratory Manual, Second Edition*, Cold Spring Harbor Laboratory Press, Cold Spring Harbor (1989), particularly Chapter 11 and Table 11.1 therein; and also in Sambrook, J. and Russell, W., *Molecular Cloning: A Laboratory Manual, Third Edition*, Cold Spring Harbor Laboratory Press, Cold Spring Harbor (2001). As is known to those of ordinary skill in the art, conditions of temperature and ionic strength determine the "stringency" of the hybridization.

Figure 7:
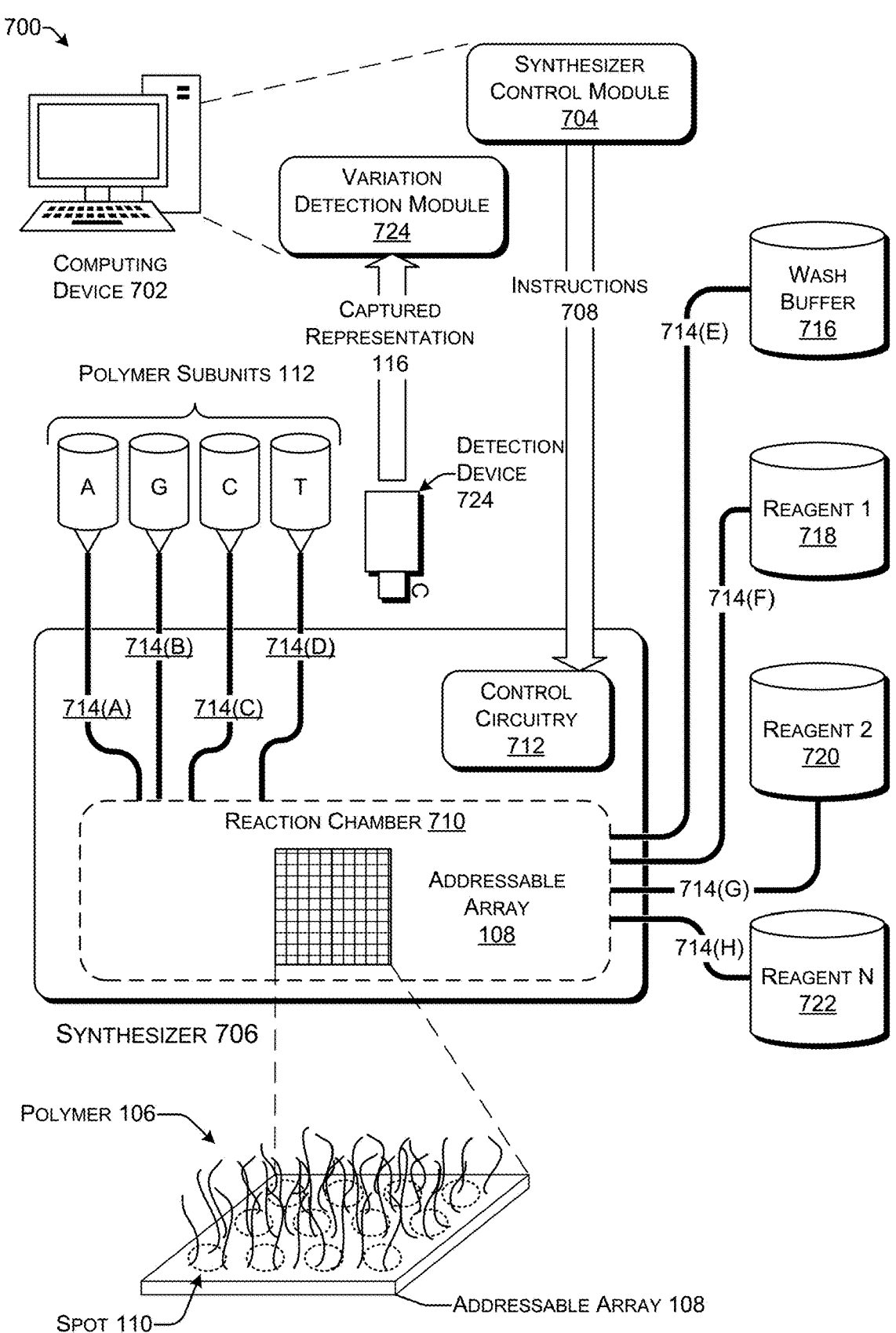
FIG. 7 is an illustrative system for implementing techniques of this disclosure.

FIG. 7 shows an illustrative system 700 that may include a computing device 702 with a synthesizer control module 704 that is communicatively connected to a synthesizer 706. The synthesizer control module 704 may provide instructions 708 that control the operation of the synthesizer 706. The instructions may cause the synthesizer 706 to create polymers 106 with specific sequences and/or that encode specific information. The computing device 702 may be implemented as any type of conventional computing device such as a desktop computer, a laptop computer, a server, a hand-held device, or the like. In an implementation, the computing device 702 may be a part of the synthesizer 706 rather than a separate device.

The synthesizer 706 is a device that selectively assembles de novo polymers 106 by spatial control of the addition of polymer subunits during solid-phase synthesis on the surface of an addressable array 104. The addressable array 104 may be formed from one or more of silicon dioxide, glass (e.g., controlled porous glass (CPG)), an insoluble polymer, a non-reactive metal such as gold, silver, or platinum, or other material. The addressable array 104 may be an electrochemically inert surface or it may include a plurality of spatially addressable microelectrodes. Thus, in an implementation, the addressable array 104 may be a microelectrode array with individually addressable electrodes that can be independently activated to vary the charge across the surface of the microelectrode array.

The addressable array 104 may be located within a reaction chamber 710 or container capable of maintaining an aqueous or predominantly aqueous environment in contact with the surface of the addressable array 104. The synthesizer 706 may also include a heater to control the temperature of the aqueous solution in the reaction chamber 710. The synthesizer 706 may also include a cooling device such as a fan or thermoelectric cooler (e.g., Peltier device) to lower the temperature of the aqueous solution in the reaction chamber 710. The synthesizer 706 may also include a heater to control the temperature of aqueous solution in the reaction chamber 710.

In one example implementation, the addressable array 104 is functionalized by spin coating with a 3 wt % solution of agarose in 1×TBE buffer for 30 s at 1500 rpm. After coating, the addressable array 104 is baked at 50° C. for 1 h. This creates a surface with functional groups that can bind to oligonucleotides or other polymers 106. To initiate synthesis, oligonucleotide sequences may be synthesized directly onto the agarose coating using standard phosphoramidite reagents and methods. After preparation by this, or another, technique, the addressable array 108 may be placed in the synthesizer 706.

Control circuitry 712 may control the operation of the synthesizer 706. The control circuitry 712 may be implemented as any type of circuitry suitable for controlling hardware devices such as a printed circuit board, microcontroller, a programmable logic controller (PLC), or the like. The control circuitry 712 receives the instructions 708 provided by the synthesizer control module 704. Instructions 708 may indicate the order of polymer subunits (e.g., nucleotides) that are to be assembled at individual spots 110 on the addressable array 108. The control circuitry 712 may be able to independently control the voltage at each electrode of a microelectrode array 108. The control circuitry 712 may also be able to activate fluid delivery pathways 714 that control movement of fluids throughout the synthesizer 706 including in the reaction chamber 710. The fluid delivery pathways 714 may be implemented by tubes and pumps, microfluidics, laboratory robotics, or other techniques known to those of ordinary skill in the art that move controlled volumes of fluids from one location to another.

Microfluidic technology facilitates the automation of chemical and biological protocols. These devices manipulate small quantities of liquid at smaller scales and with higher precision than humans. Digital microfluidic (DMF) technology is one type of flexible microfluidic technology. DMF devices manipulate individual droplets of liquids on a grid of electrodes, taking advantage of a phenomenon called electrowetting on dielectric. Activating electrodes in certain patterns can move, mix, or split droplets anywhere on the chip. Microfluidics also include full-stack microfluidics which are programmable systems that allow unrestricted combination of computation and fluidics. Examples of microfluidic technology may be found in Willsey et al., *Puddle: A dynamic, error-correcting, full-stack microfluidics platform*, Aplos'19, April 13-17, 183 (2019).

The synthesizer 706 may also include storage tanks, bottles, vials, or other containers or receptacles for storing solutions and reagents used in the synthesis of polymers 106. One such receptacle may contain a wash buffer 716. The wash buffer 716 may be used to wash unbound material from the surface of the addressable array 108. In an implementation, the wash buffer 716 may be water. In an implementation, the wash buffer 716 may be any one of a number of known aqueous buffers that are compatible with polymerases such as, for example, PBS. PBS is a water-based salt solution containing disodium hydrogen phosphate, sodium chloride and, in some formulations, may also include one or more of potassium chloride and potassium dihydrogen phosphate. Other examples of aqueous buffers known to those of ordinary skill in the art include HEPES, MOPS, PBST, TAE, TBE, TBST, TE, and TEN. See Vincent S. Stoll & John S. Blanchard, *Buffers: Principles and Practice,* 182 Meth. Enzoml., 24 (1990). The wash buffer 716 may be a mixed aqueous/organic solvent. Examples of organic solvents that may be added to a wash buffer 716 include polar, miscible organic cosolvents (e.g., DMSO, acetonitrile, etc.) which may be helpful in removing metal ions, organic residues, and denatured protein.

The synthesizer 706 may also include containers that hold one or more other reagents 718, 720, 722. These other reagents 718, 720, 722 may be any reagent used for polymer synthesis and may vary depending on the type of polymer being synthesized and the specific synthetic technique. The other reagents may include, for example, ligase, metal cofactors, anchors, linkers, etc.

In an implementation, the synthesizer 706 may include multiple containers each with a different polymer subunit 112. The polymer subunits 112 may also include physically detectable tags 104. If the polymers 106 are oligonucleotides, each species of nucleotide may be stored in a separate container. If synthesizing DNA, the nucleotides may be dNTPs that include one of the natural bases adenine (A), guanine (G), cytosine (C), or thymine (T). If synthesizing RNA, the nucleotides may be NTPs that include one of the natural bases adenine (A), guanine (G), cytosine (C), or uracil (U). The nucleotides may be modified to include a blocking group such as a 3'-OH blocking group and may also have a fluorophore.

Although four different types of nucleotides are illustrated in FIG. 7, the synthesizer 706 may include fewer types (e.g., omit one of the standard nucleotides) or more types (e.g., include one or more artificial nucleotides). Only one species of nucleotide is provided during each cycle of synthesis to control which nucleotide is next incorporated by a template-independent polymerase into the oligonucleotides. However, different ones of the available nucleotides may be introduced during different cycles of synthesis to create a plurality of oligonucleotides at different spots 110 each with a different nucleotide sequence.

There are multiple different techniques contemplated for controlling polymerization at individual spots 110 on the addressable array 108. As discussed above, the addressable array 108 may be a microelectrode array with individually addressable electrodes that are controlled by the control circuitry 712.

Spatial control of the activation of chemical activity at individual spots 110 may be also achieved by use of a targeted fluid deposition instrument such as a chemical inkjet printing device or precision laboratory robotics that can precisely apply small volumes of chemical reagents to specific locations on the surface of the addressable array 108. Chemical inkjet printing uses techniques similar to conventional printing to place nanoliter volumes of reagents at specified locations on a two-dimensional surface. Techniques for using inkjet printing to precisely deliver chemical reagents to selected locations on a surface of an array are well-known to those of ordinary skill in the art. See Paul Calvert, *Inkjet Printing for Materials and Devices*, 13(10) Chem. Mater. 3299 (2001). Chemicals such as acids or bases deposited by the targeted fluid deposition instrument may be used to cleave a chemically labile linker or a chemically labile blocking group.

A light source may also be used to provide spatial control of activation of spots 110 on the addressable array 108. Light from the light source may be directed or focused by the control circuitry 712 onto the surface of the addressable array 108 by optoelectronics such as a photomask or digital micromirror device (DMD). One example of a DMD that directs light onto an array surface is provided in Howon Lee et al., Photon-directed multiplexed enzymatic DNA synthesis for molecular digital data storage, *Nat. Comm.*, (2020) 11:5246. The light source generates light of a specific wavelength or range of wavelengths. Light from the light source may be used to excite a photo-sensitive molecule that may cleave a photolabile linker or remove a photolabile blocking group.

The synthesizer 706 also includes one or more detection devices 724 that detect the presence or absence of physically detectable tags on the surface of the addressable array 108. The specific type of detection device may be selected based on the detectible characteristics of the physically detectable tags. For example, if the physically detectable tags are fluorophores, an excitation source and a camera may be used to detect the tags such as in fluorescent microscopy. The camera may detect a range of colors or may be monochromatic only detecting variations in intensity of luminance. Techniques for detecting fluorescent tags are known to those of ordinary skill in the art and any suitable technique may be used. If the physically detectable tags are redox probes, the detection device 724 may be a potentiostat and microelectrode array that generate a voltammogram.

The detection device 724 generates a captured representation 116 of the addressable array 108 indicated where the physically detectable tags are detected. The captured representation 116 may be, for example, an image captured by fluorescent microscopy or a map of voltages detected at the electrodes in a microelectrode array.

The captured representation 116 is analyzed by a variation detection module 724 in the computing device 702. The variation detection module 724 may also be located in a different computing device 702. Variations are detected by the variation detection module 724 through comparing the plurality of locations on the addressable array where the physically detectable tags are detected to expected locations. The expected locations are based on preexisting data specifying sequences of the plurality of polymers and the specific polymer sequence assigned to be synthesized on each spot 110. For example, if fluorescence is expected at an individual spot 110 on the addressable array 108 but the captured representation 116 does not show fluorescence at that location, the variation detection module 724 may determine that a variation exists at that spot 110.

The presence of variations as detected by the variation detection module 724 may be provided to the synthesizer control module 704. The synthesizer control 704 module may then cause the synthesizer 706 to take some remedial action. For example, the synthesizer control module may send instructions 708 to the control circuitry 712 that cause the synthesizer 706 to add one of the polymer subunits 112 by opening the appropriate fluid delivery pathway 714. Variations detected by the variation detection module 724 may also be recorded by the computing device 702 and saved in association with data describing the plurality of polymers. Additionally or alternatively, if the number or frequency of variations detected by the variation detection module 724 exceeds a threshold, the synthesizer control module 704 may cause the synthesizer 706 to abort the synthesis run and discard the polymers 106.

Illustrative Computer Architecture

Figure 8:
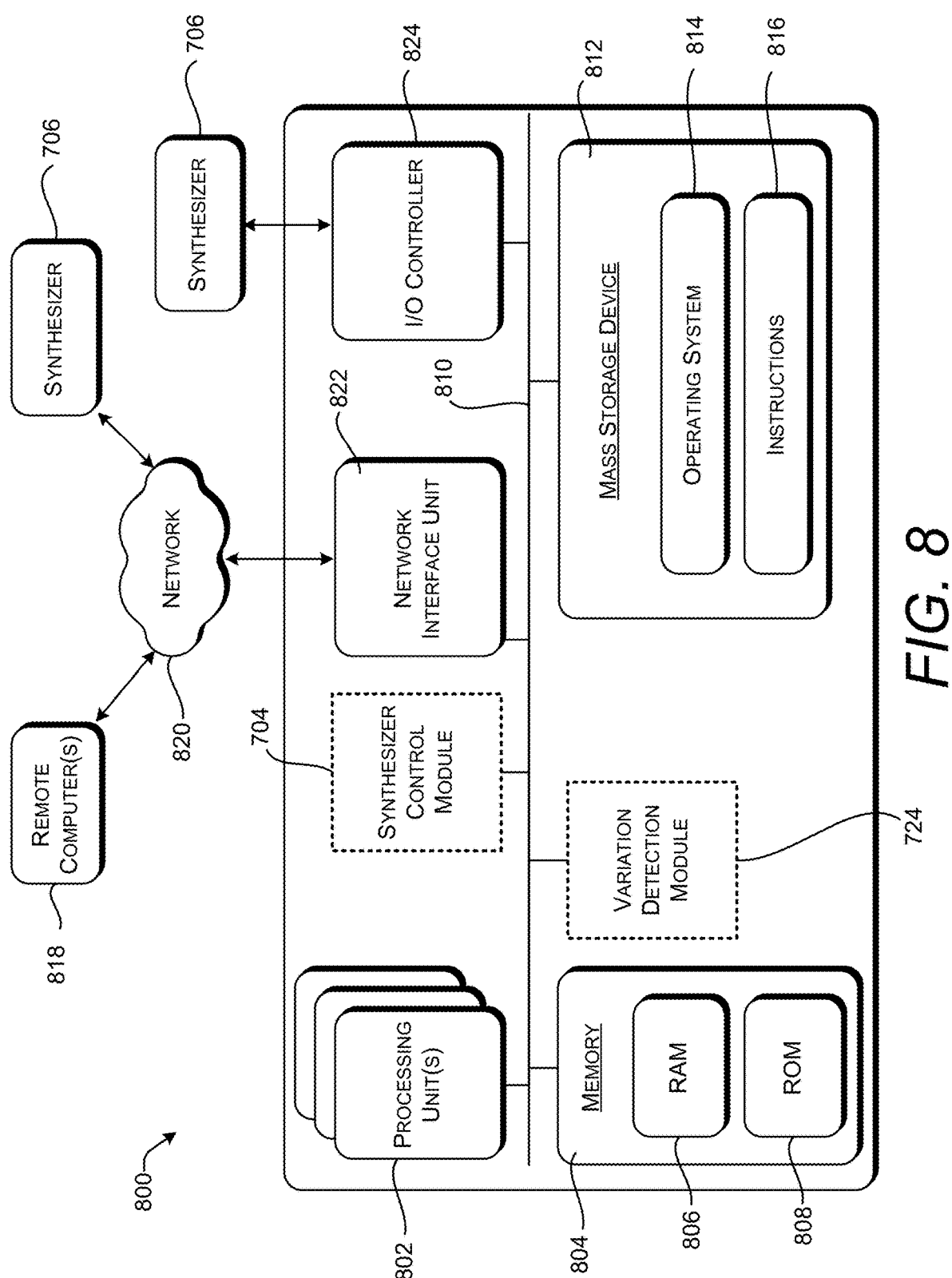
FIG. 8 is an illustrative computer architecture for implementing techniques of this disclosure.

FIG. 8 is a computer architecture diagram showing an illustrative computer hardware and software architecture for a computing device such as the computing device 702 introduced FIG. 7. In particular, the computer 800 illustrated in FIG. 8 can be utilized to implement the synthesizer control module 704 and the variation detection module 724.

The computer 800 includes one or more processing units 802, a system memory 804, including a random-access memory 806 ("RAM") and a read-only memory ("ROM") 808, and a system bus 810 that couples the memory 804 to the processing unit(s) 802. A basic input/output system ("BIOS" or "firmware") containing the basic routines that help to transfer information between elements within the computer 800, such as during startup, can be stored in the ROM 808. The computer 800 further includes a mass storage device 812 for storing an operating system 814 and other instructions 816 that represent application programs and/or other types of programs such as, for example, instructions to implement the synthesizer control module 704 and the variation detection module 724. The mass storage device 812 can also be configured to store files, documents, and data.

The mass storage device 812 is connected to the processing unit(s) 802 through a mass storage controller (not shown) connected to the bus 810. The mass storage device 812 and its associated computer-readable media provide non-volatile storage for the computer 800. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 800.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules, or other data. For example, computer-readable storage media includes, but is not limited to, RAM 806, ROM 808, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 800. For purposes of the claims, the phrase "computer-readable storage medium," and variations thereof, does not include waves or signals per se or communication media.

According to various configurations, the computer 800 can operate in a networked environment using logical connections to a remote computer(s) 818 through a network 820. The computer 800 can connect to the network 820 through a network interface unit 822 connected to the bus 810. It should be appreciated that the network interface unit 822 can also be utilized to connect to other types of networks and remote computer systems. The computer 800 can also include an input/output controller 824 for receiving and processing input from a number of other devices, including a keyboard, mouse, touch input, an electronic stylus (not shown), or equipment such as a synthesizer 706 for synthesizing polymers. Similarly, the input/output controller 824 can provide output to a display screen or other type of output device (not shown).

It should be appreciated that the software components described herein, when loaded into the processing unit(s) 802 and executed, can transform the processing unit(s) 802 and the overall computer 800 from a general-purpose computing device into a special-purpose computing device customized to facilitate the functionality presented herein. The processing unit(s) 802 can be constructed from any number of transistors or other discrete circuit elements, which can individually or collectively assume any number of states. More specifically, the processing unit(s) 802 can operate as a finite-state machine, in response to executable instructions contained within the software modules disclosed herein. These computer-executable instructions can transform the processing unit(s) 802 by specifying how the processing unit(s) 802 transitions between states, thereby transforming the transistors or other discrete hardware elements constituting the processing unit(s) 802.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 800 to store and execute the software components presented herein. It also should be appreciated that the architecture shown in FIG. 8 for the computer 800, or a similar architecture, can be utilized to implement many types of computing devices such as desktop computers, notebook computers, servers, supercomputers, gaming devices, tablet computers, and other types of computing devices known to those skilled in the art. For example, the computer 800 may be wholly or partially integrated into the synthesizer 706. It is also contemplated that the computer 800 might not include all of the components shown in FIG. 8, can include other components that are not explicitly shown in FIG. 8, or can utilize an architecture completely different than that shown in FIG. 8.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method for real-time detection of errors in de novo synthesis of a plurality of oligonucleotides, the method comprising: contacting an addressable array (108; 202) with a single species of nucleotide (212) having a blocking group and a fluorophore (214); capturing an image (116) of the addressable array (108; 202) while exciting the fluorophore (214); comparing the image to preexisting data (120) indicating locations of expected fluorescence on the addressable array (108; 202); identifying an absence or presence of fluorescence at least one location on the image (116) that corresponds to one of the locations of expected fluorescence; and in response to identifying the absence of fluorescence, contacting the addressable array (108; 202) with the single species of nucleotide (212) or saving data (128) identifying the one of the locations in association with data describing the plurality of oligonucleotides.

Clause 2. The method of clause 1, wherein the plurality of oligonucleotides are synthesized from four different species of nucleotide and the fluorophore associated with each species of nucleotide fluoresces a different color.

Clause 3. The method of clause 1 or 2, wherein the addressable array is a microelectrode array and further comprising: deprotecting oligonucleotides at a subset of locations on the microelectrode array by activating microelectrodes at the subset of locations; capturing an image of the microelectrode array while exciting the fluorophore; identifying fluorescence at a location on the image corresponding to one of the subset of locations; and in response to identifying the fluorescence, activating microelectrodes corresponding to the one of the subset of locations or saving data identifying the location in association with data describing the plurality of oligonucleotides.

Clause 4. A method for real-time detection of errors in de novo synthesis of a plurality of polymers, the method comprising: a. incorporating physically detectable tags (104) during synthesis of the plurality of polymers (106); b. detecting the physically detectable tags (104) at a plurality of locations on an addressable array (108), wherein detection of the physically detectable tags (104) indicates formation of a covalent bond or non-covalent binding; c. comparing the plurality of locations to expected locations, the expected locations based on preexisting data (120) specifying sequences of the plurality of polymers (106); d. identifying a variation (122) between the plurality of locations and the expected locations; and e. in response to identifying the variation (122), modifying synthesis of the plurality of polymers (106) or saving data (128) describing the variation in association with data describing the plurality of polymers (106).

Clause 5. The method of clause 4, wherein comparing the plurality of locations to expected locations comprises: comparing a captured representation of the addressable array showing individual ones of the plurality of locations to values generated for the individual ones of the plurality of locations from the preexisting data; and determining for each of the individual ones of the plurality of locations if the captured representation matches a corresponding value.

Clause 6. The method of clause 4 or 5, wherein the addressable array is a microelectrode array with addressable electrodes and modifying synthesis of the plurality of polymers comprises repeating activation of a subset of the addressable electrodes that were previously activated.

Clause 7. The method of clause 4 or 5, wherein the addressable array is a microelectrode array with addressable electrodes and modifying synthesis of the polymers comprises recontacting the addressable array with a species of polymer subunit that was previously added.

Clause 8. The method of any of clauses 4-7, wherein the data describing the variation is further associated with an indication of a physical container in which the plurality of polymers are stored.

Clause 9. The method of any of clauses 4-8, wherein data describing the variation includes data indicating locations of deblocking and data indicating locations of polymer subunit addition, wherein the method further comprises calculating a synthesis yield for the plurality of polymers.

Clause 10. The method of any of clauses 4-9, wherein the physically detectable tags include fluorophores, the polymers are oligonucleotides, and the addressable array is a microelectrode array with addressable electrodes.

Clause 11. The method of clause 10, wherein the de novo synthesis of a plurality of polymers comprises solid-phase, enzymatic oligonucleotide synthesis.

Clause 12. The method of clause 10 or 11, wherein the detecting the physically detectable tags at a plurality of locations on an addressable array comprises detecting fluorescence at a subset of the addressable electrodes, wherein the fluorescence indicates incorporation of a nucleotide.

Clause 13. The method of clause 10 or 11, wherein the detecting the physically detectable tags at a plurality of locations on an addressable array comprises detecting a loss of fluorescence at a subset of the addressable electrodes, wherein the loss of fluorescence indicates removal of a blocking group.

Clause 14. The method of clause 10 or 11, wherein the de novo synthesis of a plurality of polymers comprises templated enzymatic oligonucleotide synthesis, the fluorophores are incorporated into template strands, and wherein detecting the physically detectable tags at a plurality of locations on an addressable array comprises detecting fluorescence at a subset of the addressable electrodes, wherein fluorescence indicates removal of quenching blocking groups.

Clause 15. The method of clause 10, wherein the de novo synthesis of a plurality of polymers comprises ligation of bit complexes.

Clause 16. The method of clause 15, wherein a first bit complex encoding a first bit comprises a first fluorophore having a first color and quencher and a second bit complex encoding a second bit comprises a second fluorophore having a second color and a quencher, wherein detecting the physically detectable tags at a plurality of locations on an addressable array comprises detecting a change in fluorescence from the first color to the second color or from the second color to the first color at a subset of the addressable electrodes, wherein the change in fluorescence indicates hybridization of a bit complex.

Clause 17. The method of clause 15, wherein the bit complexes include a fluorophore attached to a terminal phosphate, wherein detecting the physically detectable tags at a plurality of locations on an addressable array comprises detecting fluorescence, wherein fluorescence indicates hybridization of bit complexes to oligonucleotides.

Clause 18. The method of clause 15 or 17, wherein the bit complexes include a fluorophore attached to a terminal phosphate, wherein detecting the physically detectable tags at a plurality of locations on an addressable array comprises detecting loss of fluorescence, wherein loss of fluorescence indicates ligation of the bit complexes to oligonucleotides.

Clause 19. The method of any of clauses 4-18, further comprising repeating steps a-e until synthesis of the plurality of polymers is complete.

Clause 20. The method of any of clauses 4-9, wherein the physically detectable tags comprise redox probes and detecting the physically detectable tags comprises voltammetry.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method for real-time detection of errors in de novo synthesis of a plurality of oligonucleotides, the method comprising:
   (a) contacting an addressable array with a single species of nucleotide having a blocking group and a fluorophore;
   (b) capturing an image of the addressable array while exciting the fluorophore;
   (c) comparing the image to preexisting data indicating locations of expected fluorescence on the addressable array;
   (d) identifying an absence of fluorescence in at least one location on the image that corresponds to one of the locations of expected fluorescence on the addressable array; and
   (e) in response to identifying the absence of fluorescence, stopping synthesis at all array sites and discarding the plurality of oligonucleotides without completing the synthesis run.

2. The method of claim 1, wherein the plurality of oligonucleotides are synthesized from four different species of nucleotide and a fluorophore associated with each species of nucleotide fluoresces a different color.

3. The method of claim 1, wherein identifying the absence of fluorescence comprises determining that a number or frequency of spots on the addressable array with an absence of fluorescence exceeds a threshold.

4. A method for real-time detection of errors in de novo synthesis of a plurality of polymers, the method comprising:
   (a) incorporating physically detectable tags during synthesis of the plurality of polymers;
   (b) detecting the physically detectable tags at a plurality of locations on an addressable array, wherein detection of the physically detectable tags indicates formation of a covalent bond or non-covalent binding;
   (c) comparing the plurality of locations to expected locations, the expected locations are based on preexisting data specifying sequences of the plurality of polymers;
   (d) identifying a variation between the plurality of locations and the expected locations; and
   (e) in response to identifying the variation, stopping synthesis at all array sites and discarding the plurality of polymers without completing the synthesis run.

5. The method of claim 4, wherein comparing the plurality of locations to expected locations comprises:
   comparing a captured representation of the addressable array showing individual locations of the plurality of locations to values generated for the individual locations of the plurality of locations from the preexisting data; and
   determining for each of the individual locations of the plurality of locations if the captured representation matches a corresponding value.

6. The method of claim 4, wherein the addressable array is a microelectrode array with addressable electrodes and the discarding the plurality of polymers comprises activating a subset of the addressable electrodes at locations where there is the variation.

7. The method of claim 4, further comprising saving data describing the variation in association with data describing the plurality of polymers, wherein the data describing the variation is further associated with an indication of a physical container in which the plurality of polymers are stored.

8. The method of claim 4, further comprising saving data describing the variation in association with data describing the plurality of polymers, wherein the data describing the variation includes data indicating locations of deblocking and data indicating locations of polymer subunit addition, wherein the method further comprises calculating a synthesis yield for the plurality of polymers prior to discarding the plurality of polymers.

9. The method of claim 4, wherein the physically detectable tags include fluorophores, the polymers are oligonucleotides, and the addressable array is a microelectrode array with addressable electrodes.

10. The method of claim 9, wherein the de novo synthesis of a plurality of polymers comprises solid-phase, enzymatic oligonucleotide synthesis.

11. The method of claim 9, wherein detecting the physically detectable tags at a plurality of locations on an addressable array comprises detecting fluorescence at a subset of the addressable electrodes, wherein the fluorescence indicates incorporation of a nucleotide.

12. The method of claim 9, wherein the detecting the physically detectable tags at a plurality of locations on an addressable array comprises detecting a loss of fluorescence at a subset of the addressable electrodes, wherein the loss of fluorescence indicates removal of a blocking group.

13. The method of claim 9, wherein the de novo synthesis of a plurality of polymers comprises templated enzymatic oligonucleotide synthesis and the fluorophores are incorporated into template strands, wherein detecting the physically detectable tags at a plurality of locations on an addressable array comprises detecting fluorescence at a subset of the addressable electrodes, and wherein fluorescence indicates removal of quenching blocking groups.

14. The method of claim 9, wherein the de novo synthesis of a plurality of polymers comprises ligation of bit complexes.

15. The method of claim 14, wherein a first bit complex encoding a first bit comprises a first fluorophore having a first color and quencher and a second bit complex encoding a second bit comprises a second fluorophore having a second color and a quencher, wherein detecting the physically detectable tags at a plurality of locations on an addressable array comprises detecting a change in fluorescence from the first color to the second color or from the second color to the first color at a subset of the addressable electrodes, wherein the change in fluorescence indicates hybridization of a bit complex.

16. The method of claim 14, wherein the bit complexes include a fluorophore attached to a terminal phosphate, wherein detecting the physically detectable tags at a plurality of locations on an addressable array comprises detecting fluorescence, wherein fluorescence indicates hybridization of bit complexes to oligonucleotides.

17. The method of claim 14, wherein the bit complexes include a fluorophore attached to a terminal phosphate, wherein detecting the physically detectable tags at a plurality of locations on an addressable array comprises detecting loss of fluorescence, wherein loss of fluorescence indicates ligation of the bit complexes to oligonucleotides.

18. The method of claim 4, wherein the physically detectable tags comprise redox probes and detecting the physically detectable tags comprises voltammetry.

19. The method of claim 4, wherein identifying the variation comprises determining that a number or frequency of variations exceeds a threshold.

*   *   *   *   *